United States Patent
Seto et al.

(10) Patent No.: US 7,030,107 B2
(45) Date of Patent: Apr. 18, 2006

(54) FUSED BICYCLIC PYRIDINE DERIVATIVES AS TACHYKININ RECEPTOR ANTAGONISTS

(75) Inventors: Shigeki Seto, Tochigi (JP); Asao Tanioka, Saitama (JP); Makoto Ikeda, Ibaraki (JP); Shigeru Izawa, Tochigi (JP)

(73) Assignee: Kyorin Pharmaceutical.Co., Ltd., Toyko (JP)

( * ) Notice: Subject to any disclaimer, the term of this patent is extended or adjusted under 35 U.S.C. 154(b) by 0 days.

(21) Appl. No.: 10/498,089

(22) PCT Filed: Dec. 6, 2002

(86) PCT No.: PCT/JP02/12804

§ 371 (c)(1),
(2), (4) Date: Jun. 10, 2004

(87) PCT Pub. No.: WO03/050123

PCT Pub. Date: Jun. 19, 2003

(65) Prior Publication Data

US 2005/0107375 A1    May 19, 2005

(30) Foreign Application Priority Data

Dec. 10, 2001 (JP) ............................ 2001-375173

(51) Int. Cl.
C07D 498/04 (2006.01)
A61K 31/4353 (2006.01)
A61K 31/4545 (2006.01)
A61P 1/02 (2006.01)
A61P 19/02 (2006.01)

(52) U.S. Cl. .............................. 514/211.05; 514/234.2; 514/302; 540/455; 540/490

(58) Field of Classification Search .............. 540/455, 540/490; 514/211.05, 234.2, 302
See application file for complete search history.

(56) References Cited

U.S. PATENT DOCUMENTS 6,147,071 A    11/2000    Natsugari et al.

FOREIGN PATENT DOCUMENTS

| EP | 652218 | 5/1995 |
|---|---|---|
| WO | 97/24356 | 7/1997 |

*Primary Examiner*—Bruck Kifle
(74) *Attorney, Agent, or Firm*—Wenderoth, Lind & Ponack, L.L.P.

(57) ABSTRACT

A novel fused bicyclic pyridine derivative or a salt thereof that acts as a tachykinin receptor antagonist, in particular as an NK1 receptor antagonist, is represented by the following general formula (1):

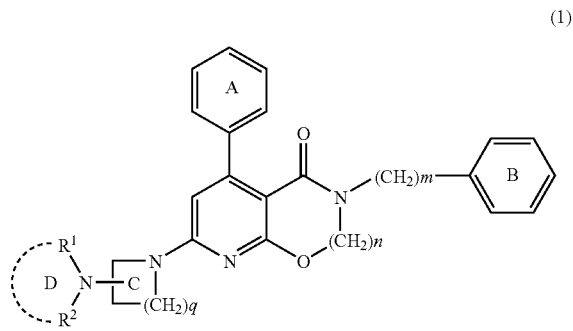

(1)

wherein the rings A and B are each a benzene ring which may have 1 to 3 substituents (any adjacent two of which may be bound to one another to form a ring);
the ring C is a nitrogen-containing ring having a hydrogen atom substituted with a nitrogen atom;
$R^1$ and $R^2$ are each independently a hydrogen atom, a $C_1$ to $C_6$ alkyl group, a $C_1$ to $C_6$ alkylsulfonyl group, a $C_1$ to $C_6$ alkylcarbonyl group, or a $C_1$ to $C_6$ alkoxycarbonyl group, or $R^1$ and $R^2$ are bound to one another to form the ring D; m is 1 or 2; n is 2 or 3; and q is an integer from 1 to 4.

15 Claims, No Drawings

FUSED BICYCLIC PYRIDINE DERIVATIVES AS TACHYKININ RECEPTOR ANTAGONISTS

TECHNICAL FIELD

The present invention relates to novel fused bicyclic pyridine derivatives that act as tachykinin receptor antagonists, as well as to pharmaceutically acceptable salts, hydrates, and solvates thereof. The present invention also relates to pharmaceutical use of such compounds.

TECHNICAL BACKGROUND

'Tachykinin' is a collective term for such neuropeptides as substance P, neurokinin A, and neurokinin B. Tachykinins are known to exhibit various physiological activities by binding to respective receptors (neurokinin 1 (NK1), neurokinin 2 (NK2), and neurokinin 3 (NK3)) present in a human body. Of different tachykinins, substance P, aside from its role as a neurotransmitter in primary sensory neurons in central and peripheral nervous systems, brings about various physiological effects, such as diuresis, excitation of neurons, increased blood vessel permeability, blood vessel dilation, contraction of smooth muscles, and immune activities. Substance P is also believed to play significant roles in the onset of various pathological conditions, such as pollakiuria, incontinence, vomiting, inflammation, allergies, respiratory tract disorders, pains, and central nervous system disorders. Accordingly, a need exists for the development of a compound that acts as a tachykinin receptor antagonist, in particular as an NK1 receptor antagonist, and is therefore suitable for use as an effective prophylactic or therapeutic agent against various pathological conditions such as those mentioned above. It is also desired that such a compound offer high safety, persistence of efficacy, and other advantageous characteristics.

At present, the following compounds are known as NK1 receptor antagonists and are described in the following publications:

(1) European Patent Application Publication No. EP-A-429366 describes compounds such as the one represented by the following formula:

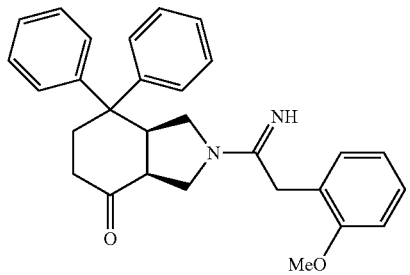

(2) International Patent Publication No. WO91/09844 describes compounds such as the one represented by the following formula:

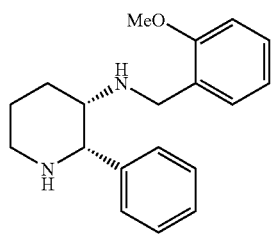

(3) European Patent Application Publication No. EP-A-532456 describes compounds such as the one represented by the following formula:

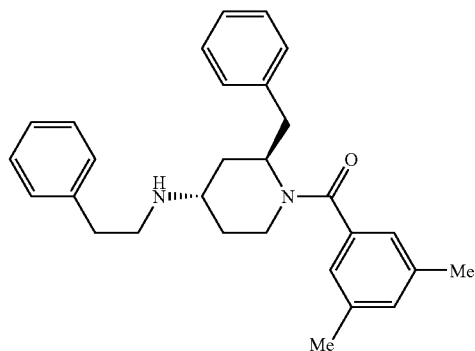

(4) European Patent Application Publication No. EP-A-522808 describes compounds such as the one represented by the following formula:

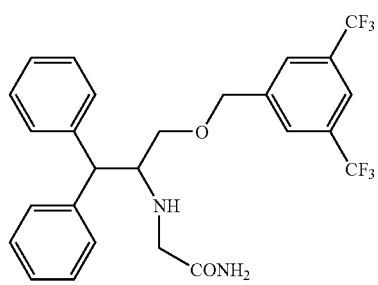

(5) International Patent Publication No. WO93/01169 describes compounds such as the one represented by the following formula:

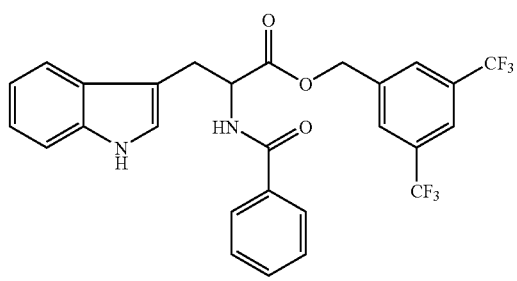

(6) Japanese Patent Laid-Open Publication No. Hei 8-67678 describes a compound represented by the following formula and salts thereof:

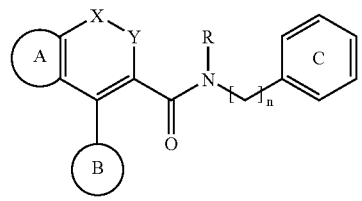

wherein the rings A and B are each a homocyclic or heterocyclic ring with at least one of the rings A and B being a heterocyclic ring; the ring C is a benzene ring; R is H or a hydrocarbon residue; one of X and Y is —NR¹— (where R¹ is H or a hydrocarbon residue) or —O— and the other is —CO— or —CS—, or one of X and Y is —N= and the other is =CR²— (where R² is H, a halogen, a hydrocarbon residue, an amino or a hydroxyl group); and n is 1 or 2.

(7) Japanese Patent Laid-Open Publication No. Hei 9-104674 describes a compound represented by the following formula:

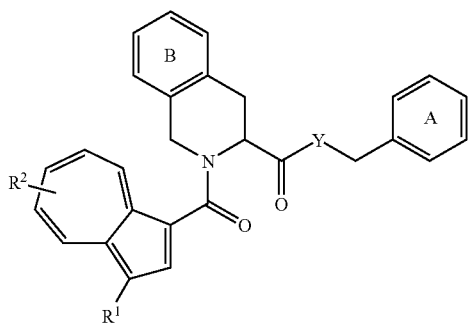

wherein X is a hydrogen or oxygen atom; Y is a nitrogen or oxygen atom which may or may not be alkylated or acylated; R¹ is a hydrogen atom, a lower alkyl group, a lower alkanoyl group, an alkyl group containing a nitrogen atom, a carbamoyl group, a lower alkylthio group, a lower alkylsulfinyl group, a lower alkylsulfonyl group, or a (4-phenylpiperadine-1-yl)methyl group; R² is a hydrogen atom, a lower alkyl group, a lower alkyl group containing a hydroxyl group, a lower alkanoyl group, or a lower alkoxy group; and the rings A and B are each a substituted or unsubstituted benzene ring.

(8) Japanese Patent Laid-Open Publication No. Hei 9-263585 describes a compound represented by the following formula:

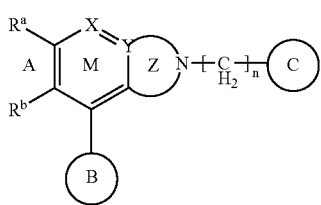

wherein the ring M is a heterocyclic ring in which the structural moiety —X=Y< is —N=C<, —CO—N<, or —CS—N<; Ra and Rb may together form the ring A, or Ra and Rb are each independently a hydrogen atom or a substituent of the ring M; the rings A and B are each independently a substituted or unsubstituted homocyclic or heterocyclic ring, provided that at least one of the rings A and B is a substituted or unsubstituted heterocyclic ring; the ring C is a substituted or unsubstituted homocyclic or heterocyclic ring; the ring Z is a substituted or unsubstituted ring; and n is an integer from 1 to 6.

(9) Japanese Patent Laid-Open Publication No. Hei 11-246559 describes a compound represented by the following formula:

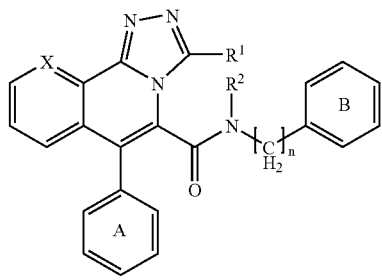

wherein X is a nitrogen atom or a CH group; R¹ is a hydrogen atom, a lower alkyl group, an aryl group, or an aralkyl group; R² is a hydrogen atom or a lower alkyl group; the rings A and B are each independently a substituted or unsubstituted benzene ring; and n is 1 or 2.

(10) Japanese Patent Laid-Open Publication No. 2000-139834 describes a compound represented by the following formula:

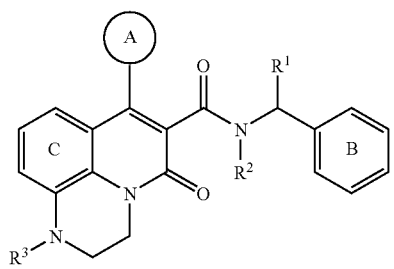

wherein R¹ and R² are each independently a hydrogen atom or an C₁ to C₆ alkyl group; R³ is a hydrogen atom, a substituted or unsubstituted C₁ to C₆ alkylcarbonyl group, a substituted or unsubstituted C₁ to C₆ alkylsulfonyl group, a substituted or unsubstituted C₁ to C₆ alkyl group, a substituted or unsubstituted arylmethyl group or an alkoxycarbonyl group; the ring A is a homocyclic or heterocyclic ring which may include 1 through 3 independently selected substituents (any adjacent two of which may be bound to one another to form a ring); the ring B is a benzene ring which may include 1 through 5 substituents (any adjacent two of which may be bound to one another to form a ring); and the ring C is a benzene ring which may include 1 through 3 substituents (any adjacent two of which may be bound to one another to form a ring).

(11) Japanese Patent Laid-Open Publication No. 2000-247957 describes a compound represented by the following formula:

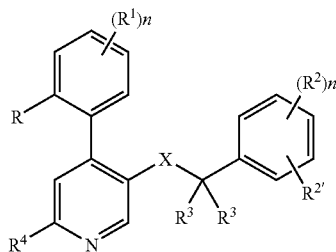

wherein R is a hydrogen atom or the like; $R^1$ is a hydrogen atom or the like; $R^2$ and $R^{2'}$ are each a hydrogen atom or the like; $R^3$ is a hydrogen atom or the like; $R^4$ is a hydrogen atom or the like; $R^5$ is a hydrogen atom or the like; $R^6$ is a hydrogen atom or the like; X is —C(O)N($R^5$)— or the like; n is an integer from 0 to 4; and m is 1 or 2.

(12) International Patent Publication No. WO0050401 describes a compound represented by the following formula:

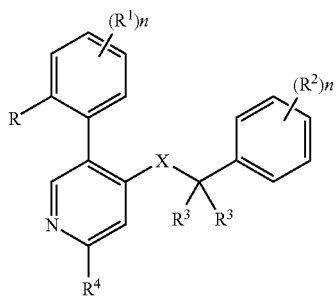

wherein R is a hydrogen atom or the like; $R^1$ is a hydrogen atom or the like; $R^2$ is a hydrogen atom or the like; $R^3$ is a hydrogen atom or the like; $R^4$ is a hydrogen atom or the like; $R^5$ is a hydrogen atom or the like; $R^6$ is a hydrogen atom or the like; X is —C(O)N($R^5$)— or the like; n is an integer from 0 to 4; and m is 1 or 2.

(13) International Patent Publication No. WO0073279 describes a compound represented by the following formula:

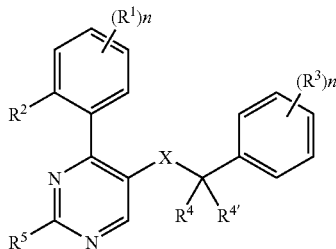

wherein $R^1$ is a hydrogen atom or the like; $R^2$ is a hydrogen atom or the like; $R^3$ is a hydrogen atom or the like; $R^4$ and $R^{4'}$ are each a hydrogen atom or the like; $R^5$ is a lower alkyl group or the like; n is an integer from 0 to 2; and X is —C(O)N($R^{4''}$)— or the like.

(14) International Patent Publication No. WO0073278 describes a compound represented by the following formula:

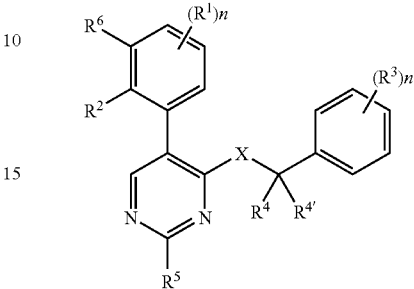

wherein $R^1$ is a hydrogen atom or the like; $R^2$ is a hydrogen atom or the like; $R^3$ is a hydrogen atom or the like; $R^4$ and $R^{4'}$ are each a hydrogen atom or the like; $R^5$ is a lower alkyl group or the like; $R^6$ is a hydrogen atom or the like; n is an integer from 0 to 2; and X is —C(O)N($R^{4''}$)— or the like.

DISCLOSURE OF THE INVENTION

At present, no effective tachykinin antagonists (in particular, NK1 receptor antagonists) have been discovered that can serve as prophylactic or therapeutic agents against the above-described pathological conditions and at the same time meet requirements for pharmaceutical products, including safety, persistence of efficacy, pharmacokinetics, and pharmacological activities.

It is thus an objective of the present invention to provide a novel compound that acts as an effective tachykinin receptor antagonist, in particular as an NK1 receptor antagonist, and can thus serve as a prophylactic or a therapeutic agent against various pathological conditions that involve tachykinin receptors, including increased urinary frequency, incontinence of urine, vomiting, inflammation, allergies, respiratory tract disorders, pains, and central nervous system disorders.

The present inventors have discovered that fused bicyclic pyridine derivatives that are represented by the following general formula (1), or salts thereof, can act as effective tachykinin receptor antagonists (in particular as NK1 receptor antagonists):

(General Formula (1))

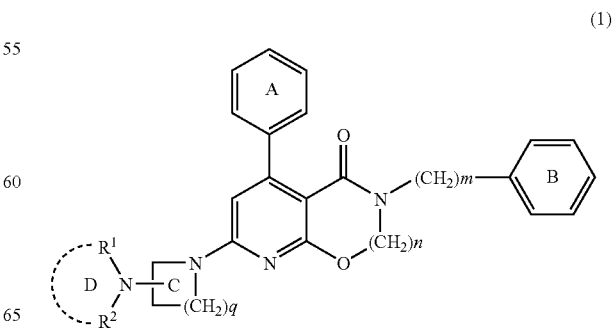

(1)

wherein the rings A and B are each a benzene ring which may include 1 through 3 substituents (any adjacent two of which may be bound to one anther to form a ring); the ring C is a nitrogen-containing ring having a hydrogen atom substituted with a nitrogen atom; $R^1$ and $R^2$ are each independently a hydrogen atom, a $C_1$ to $C_6$ alkyl group, a $C_1$ to $C_6$ alkylsulfonyl group, a $C_1$ to $C_6$ alkylcarbonyl group, or a $C_1$ to $C_6$ alkoxycarbonyl group, or $R^1$ and $R^2$ may be bound to one another to form the ring D; m is 1 or 2; n is 2 or 3, and q is an integer from 1 to 4. As evidence, the present inventors have demonstrated in animal experiments that these compounds can effectively relieve dysuria, a tachykinin-mediated disorder. This discovery led the present inventors to ultimately complete the present invention.

Accordingly, the present invention provides the followings:

(I) A fused bicyclic pyridine derivative represented by the following general formula (1), or a salt thereof:

(General Formula (1))

(1)

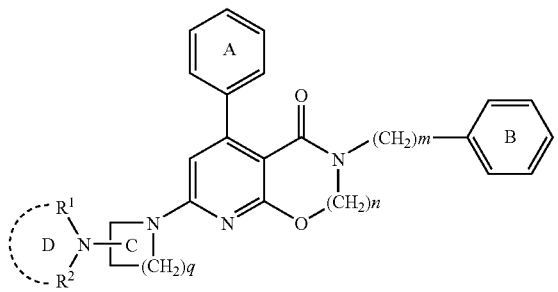

wherein the rings A and B are each a benzene ring which may have 1 to 3 substituents (any adjacent two of which may be bound to one another to form a ring) that are each independently selected from the group consisting of a halogen atom, a substituted or unsubstituted $C_1$ to $C_6$ alkyl group, and a substituted or unsubstituted $C_1$ to $C_6$ alkoxy group;

the ring C is a nitrogen-containing ring having a carbon atom substituted with a nitrogen atom;

$R^1$ and $R^2$ are each independently a hydrogen atom, a $C_1$ to $C_6$ alkyl group, a $C_1$ to $C_6$ alkylsulfonyl group, a $C_1$ to $C_6$ alkylcarbonyl group, or a $C_1$ to $C_6$ alkoxycarbonyl group, or $R^1$ and $R^2$ are bound to one another to form the ring D, which is a 3- to 7-membered non-aromatic heterocyclic ring that may contain, aside from the nitrogen atom, 1 to 3 heteroatoms selected from the group consisting of a nitrogen atom, a sulfur atom, and an oxygen atom and may further contain 1 or 2 oxo group-substituted carbon atoms;

m is 1 or 2; n is 2 or 3; and q is an integer from 1 to 4.

(II) A fused bicyclic pyridine derivative represented by the following general formula (1a), or a salt thereof:

(General Formula (1a))

(1a)

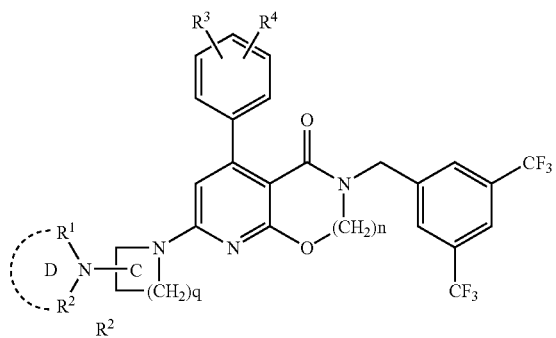

wherein $R^3$ and $R^4$ are each independently a hydrogen atom, a fluorine atom, a chlorine atom, a methyl group, an ethyl group, a trifluoromethyl group, a methoxy group, or a trifluoromethoxy group;

the ring C is a nitrogen-containing ring having a carbon atom substituted with a nitrogen atom;

$R^1$ and $R^2$ are each independently a hydrogen atom, a $C_1$ to $C_6$ alkyl group, a $C_1$ to $C_6$ alkylsulfonyl group, a $C_1$ to $C_6$ alkylcarbonyl group, or a $C_1$ to $C_6$ alkoxycarbonyl group, or $R^1$ and $R^2$ are bound to one another to form the ring D, which is a 3- to 7-membered non-aromatic heterocyclic ring that may contain, aside from the nitrogen atom, 1 to 3 heteroatoms selected from the group consisting of a nitrogen atom, a sulfur atom, and an oxygen atom and may further contain 1 or 2 oxo group-substituted carbon atoms;

n is 2 or 3; and q is an integer from 1 to 4.

(III) The fused bicyclic pyridine derivative according to (II) above or a salt thereof, wherein in the general formula (1a), n is 3.

(IV) The fused bicyclic pyridine derivative according to (II) above or a salt thereof, wherein in the general formula (1a), n is 3, and q in the ring C is 3.

(V) The fused bicyclic pyridine derivative according to (II) above or a salt thereof, wherein in the general formula (1a), n is 3, q in the ring C is 3, and the ring D is represented by the following formula:

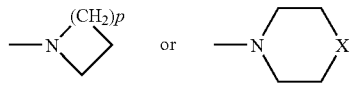

wherein p is an integer from 1 to 4, and X is an oxygen atom, a nitrogen atom, or a sulfur atom.

(VI) The fused bicyclic pyridine derivative according to (II) above or a salt thereof, wherein in the general formula (1a), n is 3, q in the ring C is 3, and the ring D is represented by the following formula:

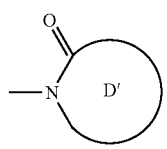

wherein the ring D' is a 3- to 7-membered cyclic amide that may contain, aside from the nitrogen atom, 1 to 3 heteroatoms selected from the group consisting of a nitrogen atom, a sulfur atom, and an oxygen atom.

(VII) The fused bicyclic pyridine derivative according to (II) above or a salt thereof, wherein in the general formula (1a), n is 3, q in the ring C is 3, and the ring D is represented by the following formula:

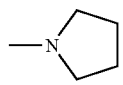

(VIII) The fused bicyclic pyridine derivative according to (II) above or a salt thereof, wherein in the general formula (1a), n is 3, q in the ring C is 3, and $R^1$ and $R^2$ are each independently a hydrogen atom, a methyl group, an ethyl group, an acetyl group, or a methylsulfonyl group.

(IX) The compound according to (II) above, wherein the compound represented by the general formula (1a) is 5-[3,5-bis(trifluoromethyl)benzyl]-6-oxo-7-phenyl-9-[4-(pyrrolidine-1-yl)piperidine-1-yl]-2,3,4,5-tetrahydro-6H-pyrido[2,3-b][1,5]oxazocine.

(X) The compound according to (II) above, wherein the compound represented by the general formula (1a) is 5-[3,5-bis(trifluoromethyl)benzyl]-7-(4-fluorophenyl)-6-oxo-9-[4-(pyrrolidine-1-yl)piperidine-1-yl]-2,3,4,5-tetrahydro-6H-pyrido[2,3-b][1,5]oxazocine.

(XI) The compound according to (II) above, wherein the compound represented by the general formula (1a) is 5-[3,5 -bis(trifluoromethyl)benzyl]-7-(2-methylphenyl)-6-oxo-9-[4-(pyrrolidine-1-yl)piperidine-1-yl]-2,3,4,5-tetrahydro-6H-pyrido[2,3-b][1,5]oxazocine.

(XII) A tachykinin receptor antagonist containing as an active ingredient the fused bicyclic pyridine derivative according to any of (I) through (XI) above or a salt thereof.

(XIII) An NK1 receptor antagonist containing as an active ingredient the fused bicyclic pyridine derivative according to any of (I) through (XI) above or a salt thereof.

(XIV) A prophylactic or therapeutic agent for dysuria, including defective bladder functions such as increased urinary frequency and incontinence of urine, containing as an active ingredient the fused bicyclic pyridine derivative according to any of (I) through (XI) above or a salt thereof.

(XV) A prophylactic or therapeutic agent for disorders of digestive tract such as ulcerative colitis and Crohn's disease, containing as an active ingredient the fused bicyclic pyridine derivative according to any of (I) through (XI) above or a salt thereof.

(XVI) A prophylactic or therapeutic agent for vomiting induced by exposure to X-ray, chemotherapy, pregnancy, migraine, postoperative pains, decreased gastrointestinal motility, and side effects of drugs, containing as an active ingredient the fused bicyclic pyridine derivative according to any of (I) through (XI) above or a salt thereof.

(XVII) A therapeutic agent for treating conditions, such as asthma, coughing, ache, migraine, tooth pain, and rheumatoid arthritis, containing as an active ingredient the fused bicyclic pyridine derivative according to any of (I) through (XI) above or a salt thereof.

BEST MODE FOR CARRYING OUT THE INVENTION

The present invention will now be described in detail.

Rings A and B

In the general formula (1), the rings A and B each represent a benzene ring, which may include 1 to 3 substituents (any adjacent two of which substituents may be bound to one another to form a ring). The substituents on each of the rings A and B may be positioned at any possible position with the number of the substituents on each ring varying from about 1 to 3. Any adjacent two of these substituents may be bound to each other to form a ring. Examples of the substituents on the rings A and B include halogen atoms, substituted or unsubstituted $C_1$ to $C_6$ alkyl groups, and substituted or unsubstituted $C_1$ to $C_6$ alkoxyl groups.

Examples of the halogen atoms include fluorine atom, chlorine atom, bromine atom and iodine atom.

Examples of the substituted or unsubstituted $C_1$ to $C_6$ alkyl groups include $C_1$ to $C_6$ alkyl groups having 1 to 3 hydrogen atoms substituted with halogen atoms. Specific examples include methyl group, ethyl group, propyl group, isopropyl group, isobutyl group, sec-butyl group, tert-butyl group, fluoromethyl group, chloromethyl group, bromomethyl group, iodomethyl group, 1-fluoroethyl group, 1-chloroethyl group, 2-chloroethyl group, difluoromethyl group, trifluoromethyl group, trichloromethyl group, and 2,2,2-trifluoroethyl group.

Examples of the substituted or unsubstituted $C_1$ to $C_6$ alkoxyl groups include $C_1$ to $C_6$ alkoxyl groups that have 1 to 3 hydrogen atoms substituted with halogen atoms. Specific examples include methoxy group, ethoxy group, propoxy group, isopropoxy group, isobutoxy group, sec-butoxy group, tert-butoxy group, fluoromethoxy group, chloromethoxy group, bromomethoxy group, iodomethoxy group, 1-fluoroethoxy group, 1-chloroethoxy group, 2-fluoroethoxy group, difluoromethoxy group, trifluoromethoxy group, trichloromethoxy group, and 2,2,2-trifluoroethoxy group.

Examples of the rings with two adjacent substituents being bound to each other to form a ring include the followings:

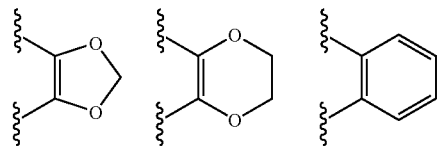

Ring A

Preferred examples of the ring A are those represented by the following formulae:

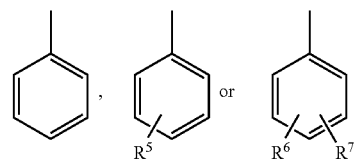

(wherein $R^5$, $R^6$, and $R^7$ are each independently a fluorine atom, a chlorine atom, a methyl group, an ethyl group, a trifluoromethyl group, a methoxy group, or a trifluoromethoxy group.)

Particularly preferred examples of the ring A are those represented by the following formulae:

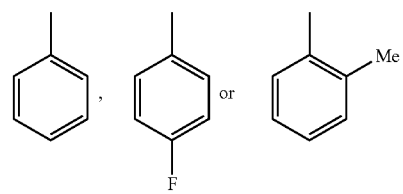

Ring B

Preferred examples of the ring B include those represented by the following formula:

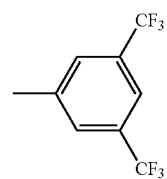

Ring C q is an integer from 1 to 4, and preferably, 3. Thus, examples of the ring C in the general formula (1) include azetidine, pyrrolidine, piperidine, and homopiperidine rings.

Preferred examples of the ring C are pyrrolidine and piperidine rings.

Particularly preferred examples of the ring C include piperidine rings.

Positions of N-Atom Substitution on Ring C

The ring C may be substituted with nitrogen atom at any possible position. When the ring C is a piperidine ring, the ring is preferably substituted at a position shown by the following formula:

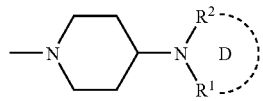

$R^1$ and $R^2$ $R^1$ and $R^2$ may be bound to each other to form the ring D or are each independently a hydrogen atom, a $C_1$ to $C_6$ alkyl group, a $C_1$ to $C_6$ alkylsulfonyl group, a $C_1$ to $C_6$ alkylcarbonyl group, or a $C_1$ to $C_6$ alkoxycarbonyl group. Examples of the $C_1$ to $C_6$ alkyl groups include methyl group, ethyl group, propyl group, isopropyl group, isobutyl group, sec-butyl group, and tert-butyl group.

Examples of the $C_1$ to $C_6$ alkylsulfonyl groups include methylsulfonyl group, ethylsulfonyl group, and propylsulfonyl group.

Examples of the $C_1$ to $C_6$ alkylcarbonyl groups include methylcarbonyl group, ethylcarbonyl group, and propylcarbonyl group.

Examples of the $C_1$ to $C_6$ alkoxycarbonyl groups include methoxycarbonyl group, ethoxycarbonyl group, propoxycarbonyl group, and tert-butoxycarbonyl group.

Ring D

The ring D represents a 3- to 7-membered nonaromatic heterocyclic ring, which may contain, aside from the nitrogen atom, 1 to 3 heteroatoms selected form the group consisting of a nitrogen atom, a sulfur atom, and an oxygen atom and may further contain 1 or 2 oxo group-substituted carbon atoms. Preferred examples are nonaromatic heterocyclic rings represented by the following formulae:

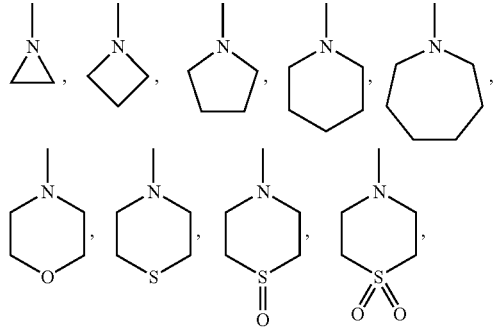

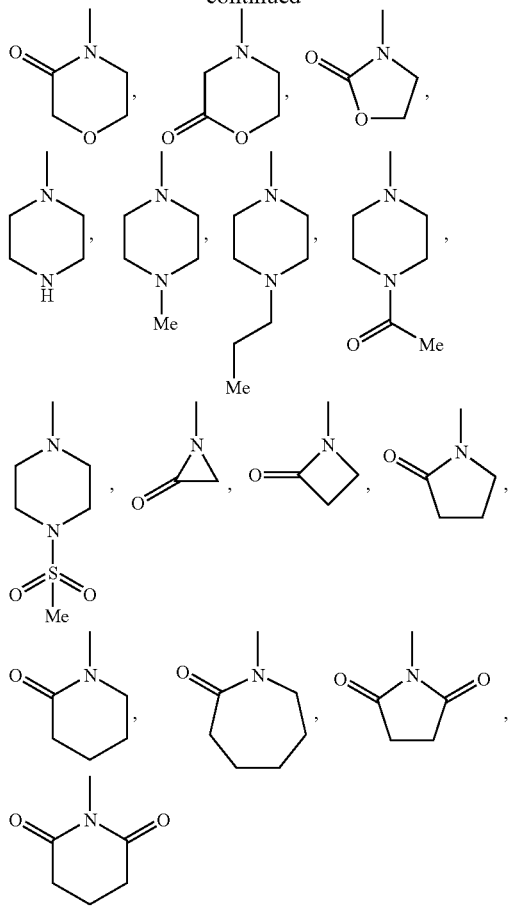

Particularly preferred are nonaromatic heterocyclic rings represented by the following formula:

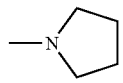

m m is 1 or 2, and preferably, 1.

n n is 2 or 3, and preferably, 3.

Preferred examples of the compounds of the present invention include 5-[3,5-bis(trifluoromethyl)benzyl]-6-oxo-7-phenyl-9-[4-(pyrrolidine-1-yl)piperidine-1-yl]-2,3,4,5-tetrahydro-6H-pyrido[2,3-b][1,5]oxazocine; 5-[3,5-bis(trifluoromethyl)benzyl]-6-oxo-7-phenyl-9-[4-(piperidine-1-yl)piperidine-1-yl]-2,3,4,5-tetrahydro-6H-pyrido[2,3-b][1,5]oxazocine; 5-[3,5-bis(trifluoromethyl)benzyl]-7-(4-chlorophenyl)-6-oxo-9-[4-(pyrrolidine-1-yl)piperidine-1-yl]-2,3,4,5-tetrahydro-6H-pyrido[2,3-b][1,5]oxazocine; 5-[3,5-bis(trifluoromethyl)benzyl]-7-(4-fluorophenyl)-6-oxo-9-[4-(pyrrolidine-1-yl)piperidine-1-yl]-2,3,4,5-tetrahydro-6H-pyrido[2,3-b][1,5]oxazocine; 5-[3,5-bis(trifluoromethyl)benzyl]-7-(2-fluorophenyl)-6-oxo-9-[4-(pyrrolidine-1-yl)piperidine-1-yl]-2,3,4,5-tetrahydro-6H-pyrido[2,3-b][1,5]oxazocine; 5-[3,5-bis(trifluoromethyl)benzyl]-7-(2- chlorophenyl)-6-oxo-9-[4-(pyrrolidine-1-yl)piperidine-1-yl]-2,3,4,5-tetrahydro-6H-pyrido[2,3-b][1,5]oxazocine; 5-[3,5-bis(trifluoromethyl)benzyl]-7-(2-methylphenyl)-6-oxo-9-[4-(pyrrolidine-1-yl)piperidine-1-yl]-2,3,4,5-tetrahydro-6H-pyrido[2,3-b][1,5]oxazocine; 5-[3,5-bis(trifluoromethyl)benzyl]-9-[4-(dimethylamino)piperidine-1-yl]-7-(2-methylphenyl)-6-oxo-2,3,4,5-tetrahydro-6H-pyrido[2,3-b][1,5]oxazocine; 5-[3,5-bis(trifluoromethyl)benzyl]-7-(2-methylphenyl)-9-[4-(morpholine-4-yl)piperidine-1-yl]-6-oxo-2,3,4,5-tetrahydro-6H-pyrido[2,3-b][1,5]oxazocine; 5-[3,5-bis(trifluoromethyl)benzyl]-7-(2-methylphenyl)-6-oxo-9-[4-(2-oxopyrrolidine-1-yl)piperidine-1-yl]-2,3,4,5-tetrahydro-6H-pyrido[2,3-b][1,5]oxazocine; 9-(4-aminopiperidine-1-yl)-5-[3,5-bis(trifluoromethyl)benzyl]-6-oxo-7-phenyl-2,3,4,5-tetrahydro-6H-pyrido[2,3-b][1,5]oxazocine; 5-[3,5-bis(trifluoromethyl)benzyl]-9-[3-(methylamino)pyrrolidine-1-yl]-6-oxo-7-phenyl-2,3,4,5-tetrahydro-6H-pyrido[2,3-b][1,5]oxazocine; 9-[4-(acetylamino)piperidine-1-yl]-5-[3,5-bis(trifluoromethyl)benzyl]-7-(2-methylphenyl)-6-oxo-2,3,4,5-tetrahydro-6H-pyrido[2,3-b][1,5]oxazocine; 5-[3,5-bis(trifluoromethyl)benzyl]-9-[4-(dimethylamino)piperidine-1-yl]-7-(4-fluorophenyl)-6-oxo-2,3,4,5-tetrahydro-6H-pyrido[2,3-b][1,5]oxazocine; 5-[3,5-bis(trifluoromethyl)benzyl]-7-(4-fluorophenyl)-9-[4-(morpholine-4-yl) piperidine-1-yl]-6-oxo-2,3,4,5-tetrahydro-6H-pyrido[2,3-b][1,5]oxazocine; 5-[3,5-bis(trifluoromethyl)benzyl]-7-(4-fluorophenyl)-6-oxo-9-[4-(2-oxopyrrolidine-1-yl) piperidine-1-yl]-2,3,4,5-tetrahydro-6H-pyrido[2,3-b][1,5] oxazocine; 5-[3,5-bis(trifluoromethyl)benzyl]-7-(2-methoxyphenyl)-6-oxo-9-[4-(pyrrolidine-1-yl)piperidine-1-yl]-2,3,4,5-tetrahydro-6H-pyrido[2,3-b][1,5]oxazocine; 4-[3,5-bis(trifluoromethyl)benzyl]-6-(2-methylphenyl)-5-oxo-8-[4-(pyrrolidine-1-yl)piperidine-1-yl]-2,3,4,5-tetrahydropyrido[3,2-f][1,4]oxazepine; 4-[3,5-bis(trifluoromethyl)benzyl]-6-(2-methylphenyl)-8-[4-(morpholine-4-yl)piperidine-1-yl]-5-oxo-2,3,4,5-tetrahydropyrido[3,2-f][1,4]oxazepine; 4-[3,5-bis(trifluoromethyl)benzyl]-6-(2-methylphenyl)-8-[4-(2-oxopyrrolidine-1-yl)piperidine-1-yl]-5-oxo-2,3,4,5 -tetrahydropyrido[3,2-f][1,4]oxazepine; 9-[4-(acetylamino)piperidine-1-yl]-5-[3,5-bis(trifluoromethyl)benzyl]-7-(4-fluorophenyl)-6-oxo-2,3,4,5-tetrahydro-6H-pyrido[2,3-b][1,5]oxazocine; and 9-[4-(methylsulfonylamino)piperidine-1-yl]-5-[3,5-bis(trifluoromethyl)benzyl]-7-(4-fluorophenyl)-6-oxo-2,3,4,5-tetrahydro-6H-pyrido[2,3-b][1,5]oxazocine.

Salts

Examples of pharmaceutically acceptable salts of the compounds of the present invention include those formed with inorganic acids, such as hydrochloric acid, hydrobromic acid, sulfuric acid, and nitric acid, and those formed with organic acids, such as acetic acid, maleic acid, fumaric acid, succinic acid, lactic acid, malic acid, tartaric acid, citric acid, methanesulfonic acid, p-toluenesulfonic acid, salicylic acid, stearic acid, and palmitic acid.

Aside from racemic mixtures, the compounds of the present invention or salts thereof may be provided in the form of optically active forms, stereoisomers, or atropisomers.

The compounds of the present invention or salts thereof may also exist in the form of hydrates or solvates. The present invention encompasses any hydrates or solvates formed by the fused bicyclic pyridine derivatives of the general formula (1a), including the preferred compounds specifically mentioned above, or salts thereof. Examples of the solvents that can form solvates include methanol, ethanol, isopropanol, acetone, ethyl acetate, methylene chloride, and diisopropylether.

Various synthetic techniques may be used to produce the compounds of the present invention. One commonly-used production process of the compounds of the present invention or salts thereof is as follows:

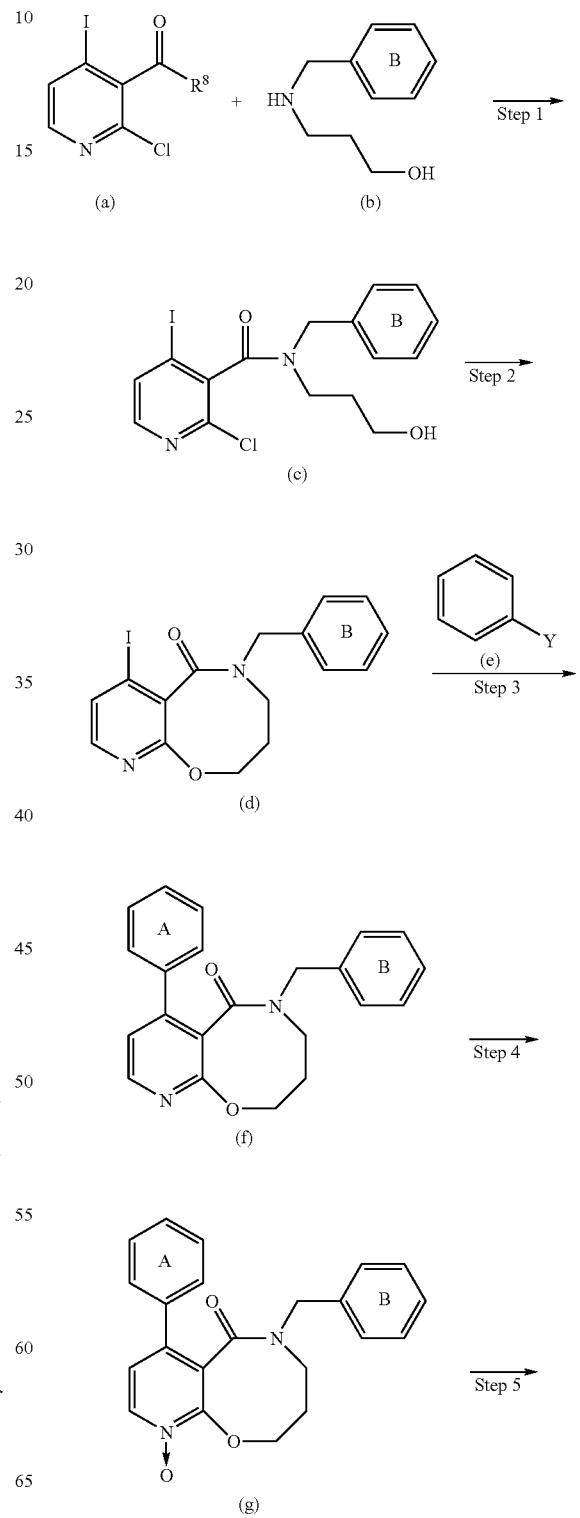

-continued

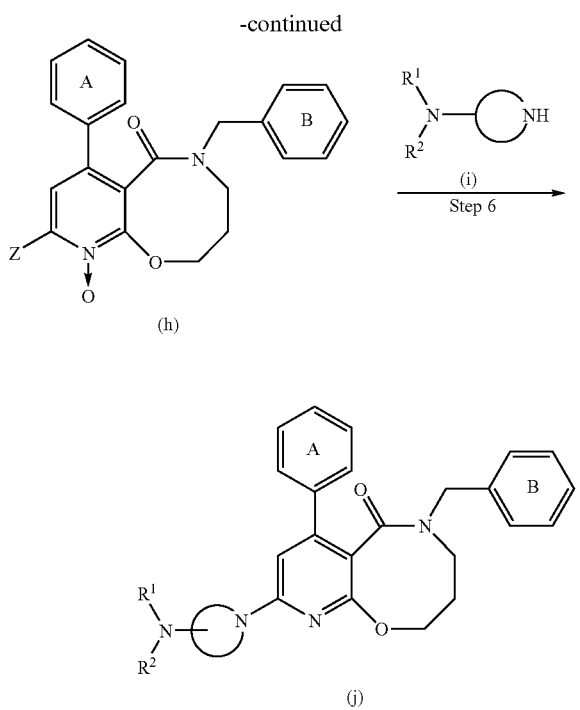

(Step 1)

In this step, a compound (a) (wherein $R^8$ represents a hydroxyl group, a halogen atom, a 1-imidazolyl group, a 4-nitrophenoxy group, an imidoyloxy succinate group, a $C_1$ to $C_6$ alkoxyl group, a benzyloxy group, or the like) and a compound (b) (wherein the ring B is as described above) are allowed to undergo condensation to generate a compound (c) (wherein the ring B is as described above). When $R^8$ is a hydroxyl group, a suitable condensation agent for use in the condensation reaction in this step may be dicyclohexylcarbodiimide (DCC), 3-ethyl-1-(3-dimethylaminopropyl) carbodimide hydrochloride (EDCI), or dimethylimidazolinium chloride (DMC). These condensation agents may be added in the form of a solid product or a solution in a proper solvent. A base may be used in the condensation reaction, including alkali carbonates, such as sodium hydrogen carbonate, or potassium carbonate, and tertially amines, such as triethylamine, diisopropylethylamine, N-methylmorpholine, diazabicyclo[5.4.0]-7-undecene, pyridine, 4-dimethylaminopyridine, or 1,8-bis(dimethylamino)naphthalene. The solvent for use in the condensation reaction may be any inert solvent that is not involved in the reaction, including N,N-dimethylformamide, N,N-dimethylacetamide, dimethylsulfoxide, acetonitrile, tetrahydrofuran, dioxane, ethyl ether, dimethoxyethane, ethylacetate, and dichloromethane. The condensation reaction may be carried out at −20° C. to 80° C. When the compound (a) for use in the condensation reaction in this step is any of a halide of a carboxylic acid, an imidazolide of a carboxylic acid, or an active ester of a carboxylic acid, in which $R^8$ is a halogen atom, a 1-imidazolyl group, a 4-nitrophenoxy group or an imidoyloxy succinate group, the reaction can be carried out by allowing the reactants to react in the presence or absence of an organic base, such as triethylamine, diisopropylethylamine, pyridine or 4-dimethylaminopyridine, or an inorganic base, such as sodium hydrogen carbonate or potassium carbonate, in a solvent, such as N,N-dimethylformamide, N,N-dimethylacetamide, dimethylsulfoxide, acetonitrile, tetrahydrofuran, dioxane, ethyl ether, dimethoxyethane, ethylacetate, toluene or dichloromethane, at −20° C. to 80° C. for 30 min. to 48 hours. When $R^8$ is a $C_1$ to $C_6$ an ester residue such as an alkoxyl group and a benzyloxy group in the condensation reaction in this step, the reaction can be carried out by allowing the reactants to react in the presence or absence of trimethylaluminium or tetraisopropoxytitanium or in the presence or absence of an acidic or a basic catalyst, such as p-toluenesulfonic acid, sodium methoxide, potassium t-butoxide, or sodium hydride, in a solvent, such as N,N-dimethylformamide, N,N-dimethylacetamide, dimethylsulfoxide, acetonitrile, tetrahydrofuran, dioxane, toluene, xylene, mesitylene, pyridine, quinoline, or dichloromethane, at 15° C. to 150° C. for 30 min. to 48 hours.

(Step 2)

In this step, the compound (c) (wherein the ring B is as described above) is cyclized to generate a compound (d) (wherein the ring B is as described above). The step may be carried out by allowing the cyclization to take place in the presence or absence of an organic base, such as sodium-tert-butoxide or potassium-tert-butoxide, or an inorganic base, such as sodium hydride, potassium carbonate, sodium carbonate, cesium carbonate or sodium acetate, in a solvent, such as N,N-dimethylformamide, N,N-dimethylacetamide, dimethylsulfoxide, acetonitrile, tetrahydrofuran, dioxane, toluene, xylene, mesitylene, pyridine, quinoline, or dichloromethane, at 0° C. to 150° C. for 30 min. to 48 hours.

(Step 3)

In this step, the compound (d) (wherein the ring B is as described above) and a compound (e) (wherein the ring A is as described above, Y is a halogen atom, $OSO_2R^9$ (wherein $R^9$ is a halogen-substituted or unsubstituted $C_1$ to $C_6$ alkyl group) or $B(R^{10})_2$ ($R^{10}$ substituents are each independently a hydroxyl group, a $C_1$ to $C_6$ alkyl group, or a $C_1$ to $C_6$ alkoxyl group, or $R^{10}$ substituents may be bound to each other to form a ring)) are allowed to undergo cross-coupling in the presence of a transitional metal catalyst such as a palladium or nickel complex to generate a compound (f) (wherein the rings A and B are as described above). Preferably, the process is carried out by using an inert solvent that is not involved in the process, including N,N-dimethylformamide, N,N-dimethylacetamide, dimethylsulfoxide, acetonitrile, tetrahydrofuran, dioxane, dichloromethane, toluene, ethanol or water. These solvents may be used individually or they may be mixed in any proportion. Examples of the palladium complexes for use in the process include palladium chloride, palladium acetate, acetylacetonato palladium, and tetrakis(triphenylphosphine)palladium. Examples of the nickel complexes for use in the process include bis(acetylacetonato)nickel, bis(1,5-cyclooctadiene) nickel, and tetrakis(triphenylphosphine)nickel. Each of these palladium or nickel complexes is used in an amount of 0.001 to 1 equivalent, preferably in an amount of 0.01 to 0.1 equivalent, with respect to the compound (d). When it is desired to use a ligand for the palladium or nickel complex in the process, such a ligand may be triphenylphosphine, tri-o-tolylphosphine, tri-2-furylphosphine, 1,2-bis(diphenylphosphino)ethane, 1,1'-bis(diphenylphosphino)ferrocene, or 2,2'-bis(diphenylphosphino)-1,1'-binaphthyl. Each of these ligands is used in an amount of 0.2 to 5 equivalents, preferably in an amount of 0.3 to 3 equivalents, with respect to the palladium or nickel complex. Preferably, the process is carried out in the presence of a proper base. Among such bases are organic bases, including triethylamine, tributylamine, diisopropylethylamine, N-methylmorpholine, pyridine, lutidine, and collidine, and inorganic bases, including sodium hydrogen carbonate, sodium carbonate, potassium carbonate, calcium carbonate, cesium carbonate, and tripotassium phosphate. Each of these bases is used in an amount of 1 to 20 equivalents, preferably in an amount of 2 to 10 equivalents, with respect to the compound (d). The cross-coupling reaction in this step is carried out by allowing the reactants to undergo the reaction at 15 to 150° C., preferably at 50 to 120° C., for 30 min. to 24 hours.

(Step 4)

In this step, the compound (f) (wherein the rings A and B are as described above) is oxidized at the nitrogen on its pyridine ring to generate a compound (g) (wherein the rings A and B are as described above). The step may be carried out by using a peroxide (such as m-chloroperbenzoic acid, hydrogen peroxide, and peracetic acid) in an amount of 1 to 10 equivalents, preferably in an amount of 1 to 2 equivalents, with respect to the compound (f) and by allowing oxidization to proceed at –20° C. to 80° C., preferably at 0 to 30° C., for 30 min. to 72 hours. The solvent for use in this step may be dichloromethane, toluene, ethyl acetate, dimethoxyethane, ethyl ether, dioxane, tetrahydrofuran, acetonitrile, N,N-dimethylformamide, and N,N-dimethylacetamide.

(Step 5)

In this step, Z (wherein Z represents a halogen atom) is introduced into the compound (g) (wherein the rings A and B are as described above) with the help of the N-oxide to generate a compound (h). When Z is a chlorine atom, the step may be carried out by using such a chlorinating agent as phosphorus oxychloride, pivaloyl chloride, and oxalyl chloride in an amount of 1 to 20 equivalents, preferably in an amount of 2 to 10 equivalents, with respect to the compound (g) and by allowing the reaction to proceed at 15 to 120° C., preferably at 80 to 120° C., for 30 min. to 24 hours. When it is desired to use a base in the process, such a base may be triethylamine, tributylamine, diisopropylethylamine, N-methylmorpholine, pyridine, lutidine, or collidine. When it is desired to use a solvent, it may be any inert solvent that is not involved in the reaction, including dichloromethane, xylene, toluene, dioxane, and tetrahydrofuran.

(Step 6)

In this step, the compound (h) (wherein Z, and the rings A and B are as described above) is reacted with a compound (i) to generate a compound (j) ($R^1$, $R^2$, and the rings A and B are as described above). The reaction can be carried out by using the compound (i) in an amount of 1 to 20 equivalents of the compound (h) and allowing the reactants to react in the presence or absence of a base at 80 to 200° C., preferably at 120 to 150° C., for 30 min. to 24 hours. A base may preferably be used, including organic bases, such as trimethylamine, tributylamine, diisopropylethylamine, N-methylmorpholine, pyridine, lutidine, collidine, and N,N-dimethylaniline, and inorganic bases, such as sodium hydrogen carbonate, sodium carbonate, potassium carbonate, calcium carbonate, cesium carbonate, and tripotassium phosphate. When it is desired to use a solvent, such a solvent may be any inert solvent that is not involved in the reaction, including N,N-dimethylformamide, N,N-dimethylacetamide, sulfolane, acetonitrile, tetrahydrofuran, dioxane, xylene, toluene, ethanol and water.

The compounds (1) of the present invention can be isolated/purified by ordinary means (for example, extraction, recrystallization, distillation, and chromatography). When the resulting compounds tend to form salts, such salts can be produced by ordinary techniques or equivalent techniques (for example, neutralization).

The compounds (1) of the present invention or salts thereof act as tachykinin receptor antagonists, in particular NK1 receptor antagonists, and are thus useful as:

prophylactic or therapeutic agents for dysuria, including defective bladder functions such as increased urinary frequency and incontinence of urine;

prophylactic or therapeutic agents for disorders of digestive tract such as ulcerative colitis and Crohn's disease;

prophylactic or therapeutic agents for vomiting induced by exposure to X-ray, chemotherapy, pregnancy, migraine, postoperative pains, decreased gastrointestinal motility, and side effects of drugs;

prophylactic or therapeutic agents for vomiting induced by exposure to X-ray, chemotherapy, pregnancy, migraine, postoperative pains, decreased gastrointestinal motility, and side effects of drugs; and therapeutic agents for asthma, coughing, ache, migraine, tooth pain, rheumatoid arthritis and other conditions.

The compounds (1) of the present invention or salts thereof may be used individually, or they may be formed into pharmaceutical compositions along with one or more pharmaceutically acceptable adjuvants. Specifically, the compounds of the present invention may be mixed with pharmaceutically acceptable carriers, excipients (such as starch, lactose, calcium phosphate, and calcium carbonate), lubricants (such as magnesium stearate, calcium stearate, talc, and stearic acid), binders (such as starch, cellulose crystals, carboxymethylcellulose, gum Arabic, polyvinylpyrrolidone, and alginic acid), disintegrating agents (such as talc, and carboxymethylcellulose calcium), and diluents (such as physiological saline, and aqueous solutions of glucose, mannitol and lactose). Using ordinary techniques, the compounds of the present invention may be prepared as tablets, capsules, granules, powders, fine granules, ampules, or injections for oral or parenteral administration. While the dosage of the compounds (1) of the present invention or salts thereof may vary depending on the type of salt, route of administration, and age and conditions of patients, a typical dose for humans and other mammals, for example, is in the range of 0.0001 to 300 mg/kg/day as measured by the amount of the compounds (1) of the present invention or salts thereof. The compounds (1) or salts thereof may be administered in a single dose or several doses each day.

EXAMPLES

The present invention will now be described in detail with reference to Examples, Reference Examples, and Test Examples, as will an exemplary production process of a starting material of the compounds (1) of the present invention, which is also a novel compound. It should be appreciated that the compounds of the present invention are not limited to those described in the following examples and may be modified without departing from the scope and the spirit of the invention.

Example 1

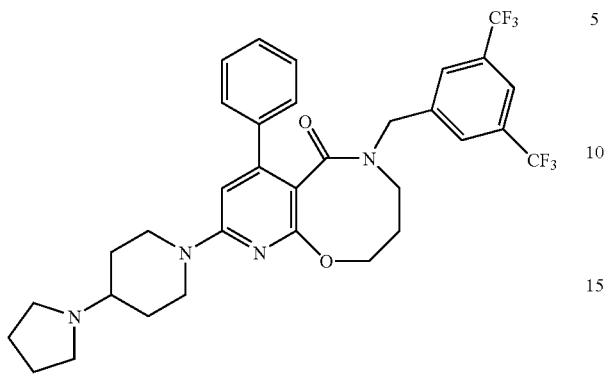

A mixture of 5-[3,5-bis(trifluoromethyl)benzyl]-9-chloro-6-oxo-7-phenyl-2,3,4,5-tetrahydro-6H-pyrido[2,3-b][1,5]oxazocine (40.0 mg) and 4-(pyrrolidine-1-yl)piperidine (30.0 mg) was stirred at 150° C. for 3 hours. To the remaining product, water was added and the mixture was extracted with ethyl acetate. The extract was then washed with a saturated aqueous solution of sodium hydrogen carbonate and was dried on anhydrous sodium sulfate. The solvent was removed and the resulting residue was purified on a silica gel column chromatography (ethyl acetate:methanol=3:1) to obtain 5-[3,5-bis(trifluoromethyl)benzyl]-6-oxo-7-phenyl-9-[4-(pyrrolidine-1-yl)piperidine-1-yl]-2,3,4,5-tetrahydro-6H-pyrido[2,3-b][1,5]oxazocine (25.0 mg, 51%).

MS (FAB$^+$)m/z: 633 (M+H$^+$) HRMS (FAB$^+$): Calcd for $C_{33}H_{35}F_6N_4O_2$: 633.2664; found: 633.2638. $^1$H-NMR (400 Mz, CDCl$_3$) ppm: 1.50–1.63 (2H, m), 1.73–1.88 (5H, m), 1.93–2.03 (2H, m), 2.13–2.33 (2H, m), 2.56–2.67 (4H, m), 2.90–3.03 (2H, m), 3.27–3.34 (1H, m), 3.86 (1H, t, J=16.7 Hz), 4.09 (1H, d, J=15.6 Hz), 4.23–4.33 (2H, m), 4.36–4.45 (1H, m), 4.45–4.53 (1H, m), 5.42 (1H, d, J=15.6 Hz), 6.37 (1H, s), 7.22–7.38 (5H, m), 7.70 (2H, s), 7.80 (1H, s)

Example 2

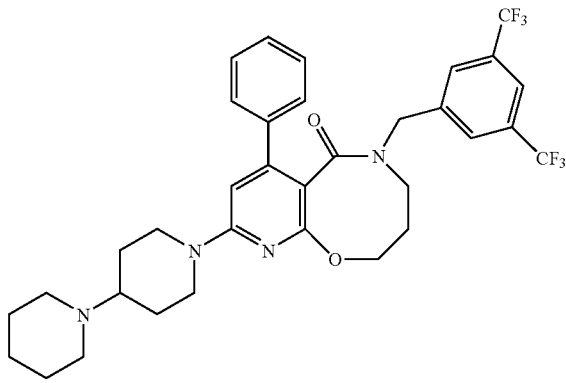

In a similar manner to Example 1, 5-[3,5-bis(trifluoromethyl)benzyl]-9-chloro-6-oxo-7-phenyl-2,3,4,5-tetrahydro-6H-pyrido[2,3-b][1,5]oxazocine (40.0 mg) was reacted with 4-(piperidine-1-yl)piperidine (32.7 mg) to obtain 5-[3,5-bis(trifluoromethyl)benzyl]-6-oxo-7-phenyl-9-[4-(piperidine-1-yl)piperidine-1-yl]-2,3,4,5-tetrahydro-6H-pyrido[2,3-b][1,5]oxazocine (24.0 mg, 48%).

MS (EI) m/z: 646 (M$^+$) HRMS (EI): Calcd for $C_{34}H_{36}F_6N_4O_2$: 646.2742; found: 646.2731.

Example 3

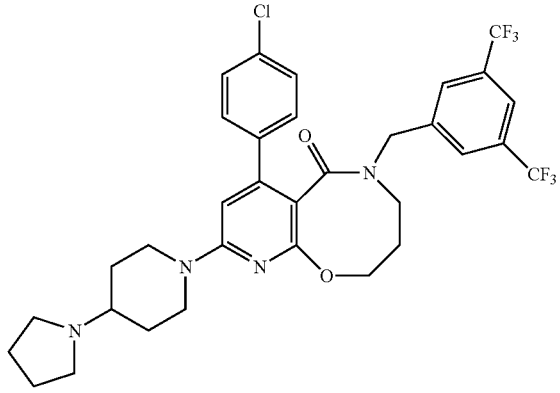

In a similar manner to Example 1, 5-[3,5-bis(trifluoromethyl)benzyl]-9-chloro-7-(4-chlorophenyl)-6-oxo-2,3,4,5-tetrahydro-6H-pyrido[2,3-b][1,5]oxazocine (100 mg) was reacted with 4-(pyrrolidine-1-yl)piperidine (70.2 mg) to obtain 5-[3,5-bis(trifluoromethyl)benzyl]-7-(4-chlorophenyl)-6-oxo-9-[4-(pyrrolidine-1-yl)piperidine-1-yl]-2,3,4,5-tetrahydro-6H-pyrido[2,3-b][1,5]oxazocine (67.4 mg, 56%).

MS (EI) m/z: 666 (M$^+$) HRMS (EI): Calcd for $C_{33}H_{33}ClF_6N_4O_2$: 666.2196; found: 666.2201.

Example 4

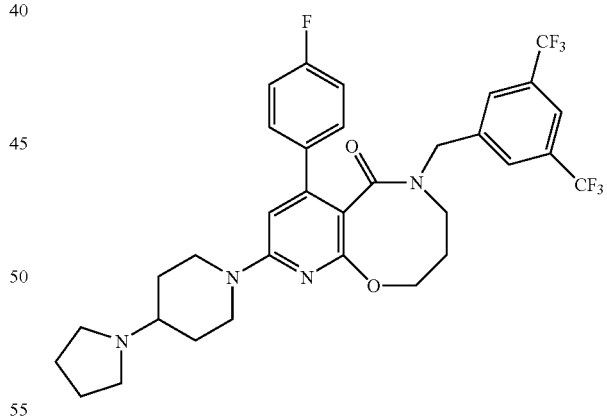

In a similar manner to Example 1, 5-[3,5-bis(trifluoromethyl)benzyl]-9-chloro-7-(4-fluorophenyl)-6-oxo-2,3,4,5-tetrahydro-6H-pyrido[2,3-b][1,5]oxazocine (100 mg) was reacted with 4-(pyrrolidine-1-yl)piperidine (68.5 mg) to obtain 5-[3,5-bis(trifluoromethyl)benzyl]-7-(4-fluorophenyl)-6-oxo-9-[4-(pyrrolidine-1-yl)piperidine-1-yl]-2,3,4,5-tetrahydro-6H-pyrido[2,3-b][1,5]oxazocine (54.7 mg, 45%).

MS (EI) m/z: 650 (M$^+$) HRMS (EI): Calcd for $C_{33}H_{33}F_7N_4O_2$: 650.2492; found: 650.2451. $^1$H-NMR (400 Mz, CDCl$_3$) ppm: 1.50–1.63 (2H, m), 1.63–1.85 (5H, m), 1.93–2.02 (2H, m), 2.13–2.32 (2H, m), 2.56–2.65 (4H, m), 2.91–3.04 (2H, m), 3.26–3.34 (1H, m), 3.83 (1H, t, J=13.7 Hz), 4.10 (1H, d, J=15.1 Hz), 4.23–4.32 (2H, m), 4.36–4.43 (1H, m), 4.46–4.53 (1H, m), 5.40 (1H, d, J=15.1 Hz), 6.33 (1H, s), 6.96–7.03 (2H, m), 7.19–7.25 (2H, m), 7.67 (2H, s), 7.81 (1H, s)

Example 5

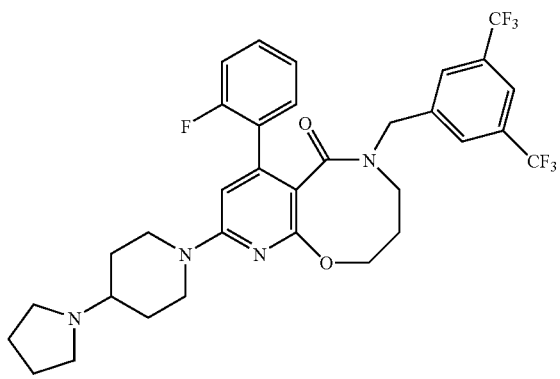

In a similar manner to Example 1, 5-[3,5-bis(trifluoromethyl)benzyl]-9-chloro-7-(2-fluorophenyl)-6-oxo-2,3,4,5-tetrahydro-6H-pyrido[2,3-b][1,5]oxazocine (100 mg) was reacted with 4-(pyrrolidine-1-yl)piperidine (70.2 mg) to obtain 5-[3,5-bis(trifluoromethyl)benzyl]-7-(2-fluorophenyl)-6-oxo-9-[4-(pyrrolidine-1-yl)piperidine-1-yl]-2,3,4,5-tetrahydro-6H-pyrido[2,3-b][1,5]oxazocine (63.4 mg, 52%).

MS (EI) m/z: 650 (M$^+$) HRMS (EI): Calcd for $C_{33}H_{33}F_7N_4O_2$: 650.2492; found: 650.2451.

Example 6

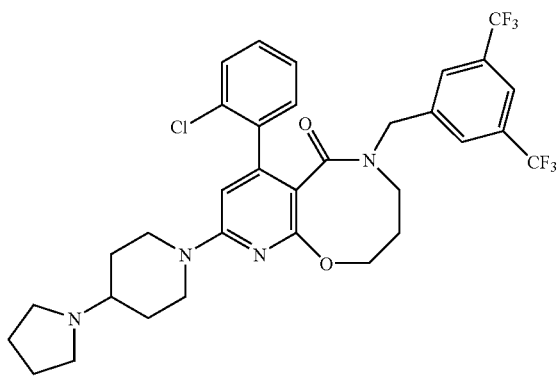

In a similar manner to Example 1, 5-[3,5-bis(trifluoromethyl)benzyl]-9-chloro-7-(2-chlorophenyl)-6-oxo-2,3,4,5-tetrahydro-6H-pyrido[2,3-b][1,5]oxazocine (100 mg) was reacted with 4-(pyrrolidine-1-yl)piperidine (70.2 mg) to obtain 5-[3,5-bis(trifluoromethyl)benzyl]-7-(2-chlorophenyl)-6-oxo-9-[4-(pyrrolidine-1-yl)piperidine-1-yl]-2,3,4,5-tetrahydro-6H-pyrido[2,3-b][1,5]oxazocine (57.7 mg, 48%).

MS (EI) m/z: 666 (M$^+$) HRMS (EI): Calcd for $C_{33}H_{33}ClF_6N_4O_2$: 666.2196; found: 666.2206.

Example 7

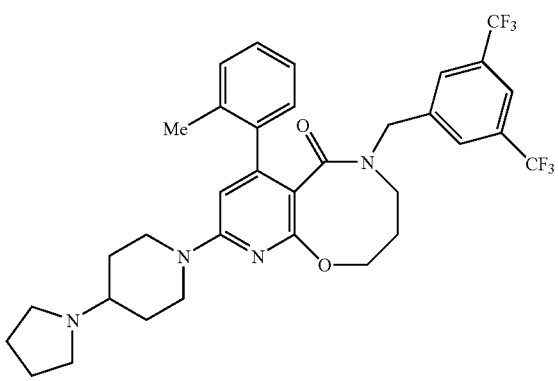

In a similar manner to Example 1, 5-[3,5-bis(trifluoromethyl)benzyl]-9-chloro-7-(2-methylphenyl)-6-oxo-2,3,4,5-tetrahydro-6H-pyrido[2,3-b][1,5]oxazocine (100 mg) was reacted with 4-(pyrrolidine-1-yl)piperidine (70.2 mg) to obtain 5-[3,5-bis(trifluoromethyl)benzyl]-7-(2-methylphenyl)-6-oxo-9-[4-(pyrrolidine-1-yl)piperidine-1-yl]-2,3,4,5-tetrahydro-6H-pyrido[2,3-b][1,5]oxazocine (58.2 mg, 48%).

MS (EI) m/z: 646 (M$^+$) HRMS (EI): Calcd for $C_{34}H_{36}F_6N_4O_2$: 646.2742; found: 646.2704. $^1$H-NMR (400 Mz, CDCl$_3$) ppm: 1.50–2.01 (10H, m), 2.04–2.20 (1H, m), 2.20–2.36 (3H, m), 2.54–2.67 (4H, m), 2.88–3.02 (2H, m), 3.11–3.23 (1H, m), 3.63–3.83 (1H, m), 3.90–3.99 (1H, m), 4.20–4.51 (4H, m), 5.32–5.43 (1H, m), 6.26 (1H, s), 6.76–7.33 (4H, m), 7.53 (2H, s), 7.76 (1H, s)

Example 8

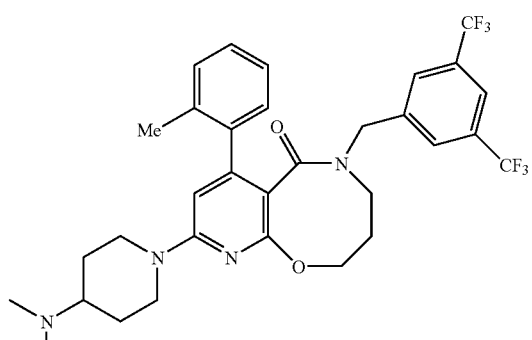

In a similar manner to Example 1, 5-[3,5-bis(trifluoromethyl)benzyl]-9-chloro-7-(2-methylphenyl)-6-oxo-2,3,4,5-tetrahydro-6H-pyrido[2,3-b][1,5]oxazocine (47.6 mg) was reacted with 4-(dimethylamino)piperidine (28.8 mg) to obtain 5-[3,5-bis(trifluoromethyl)benzyl]-9-[4-(dimethylamino)piperidine-1-yl]-7-(2-methylphenyl)-6-oxo-2,3,4,5-tetrahydro-6H-pyrido[2,3-b][1,5]oxazocine (23.1 mg, 41%).

MS (EI) m/z: 620 (M$^+$) HRMS (EI): Calcd for $C_{32}H_{34}F_6N_4O_2$: 620.2586; found: 620.2560.

Example 9

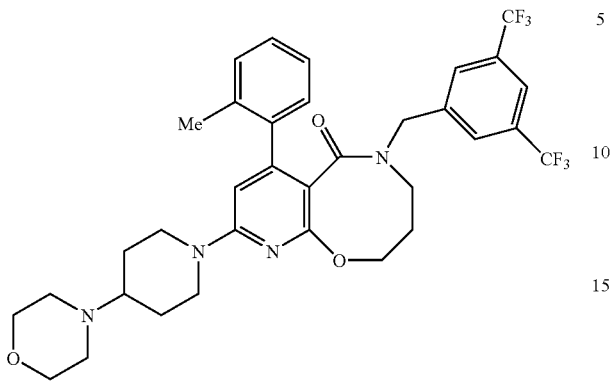

In a similar manner to Example 1, 5-[3,5-bis(trifluoromethyl)benzyl]-9-chloro-7-(2-methylphenyl)-6-oxo-2,3,4,5-tetrahydro-6H-pyrido[2,3-b][1,5]oxazocine (47.6 mg) was reacted with 4-(morpholine-4-yl)piperidine (38.3 mg) to obtain 5-[3,5-bis(trifluoromethyl)benzyl]-7-(2-methylphenyl)-9-[4-(morpholine-4-yl)piperidine-1-yl]-6-oxo-2,3,4,5-tetrahydro-6H-pyrido[2,3-b][1,5]oxazocine (24.2 mg, 41%).

MS (EI) m/z: 662 (M$^+$) HRMS (EI): Calcd for $C_{34}H_{36}F_6N_4O_3$: 662.2692; found: 662.2655. $^1$H-NMR (400 Mz, CDCl$_3$) ppm: 1.20–1.98 (5H, m), 2.03–2.20 (1H, m), 2.31 (2H, s), 2.38–2.47 (1H, m), 2.52–2.60 (4H, m), 2.83–2.95 (2H, m), 3.13–3.22 (1H, m), 3.69–3.77 (6H, m), 3.90–3.97 (1H, m), 4.27–4.50 (4H, m), 5.32–5.43 (1H, m), 6.26 (1H, s), 6.76–7.33 (4H, m), 7.53 (2H, s), 7.76 (1H, s)

Example 10

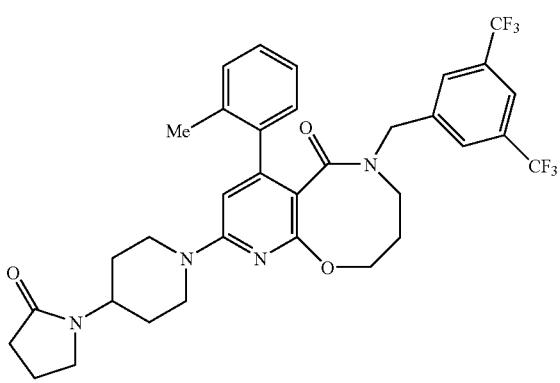

In a similar manner to Example 1, 5-[3,5-bis(trifluoromethyl)benzyl]-9-chloro-7-(2-methylphenyl)-6-oxo-2,3,4,5-tetrahydro-6H-pyrido[2,3-b][1,5]oxazocine (47.6 mg) was reacted with 4-(2-oxopyrrolidine-1-yl)piperidine (38.0 mg) to obtain 5-[3,5-bis(trifluoromethyl)benzyl]-7-(2-methylphenyl)-6-oxo-9-[4-(2-oxopyrrolidine-1-yl)piperidine-1-yl]-2,3,4,5-tetrahydro-6H-pyrido[2,3-b][1,5]oxazocine (23.1 mg, 39%).

MS (EI) m/z: 660 (M$^+$) HRMS (EI): Calcd for $C_{34}H_{34}F_6N_4O_3$: 660.2535; found: 660.2499. $^1$H-NMR (400 Mz, CDCl$_3$) ppm: 1.64–1.80 (4H, m), 1.80–1.93 (2H, m), 1.97–2.06 (2H, m), 2.06–2.20 (1H, m), 2.32 (2H, s), 2.41 (2H, t, J=7.8 Hz), 2.88–3.03 (2H, m), 3.14–3.23 (1H, m), 3.33 (2H, t, J=7.8 Hz), 3.64–3.84 (1H, m), 3.91–3.98 (1H, m), 4.19–4.68 (5H, m), 5.32–5.43 (1H, m), 6.27 (1H, s), 6.76–7.33 (4H, m), 7.53 (2H, s), 7.76 (1H, s)

Example 11

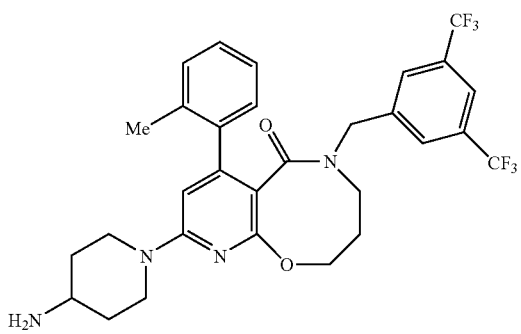

A mixture of 5-[3,5-bis(trifluoromethyl)benzyl]-9-chloro-6-oxo-7-phenyl-2,3,4,5-tetrahydro-6H-pyrido[2,3-b][1,5]oxazocine (40.0 mg) and 4-(t-butoxycarbonylamino)piperidine (38.9 mg) was stirred at 140° C. for 5 hours. To the remaining product, water was added and the mixture was extracted with ethyl acetate, followed by drying on anhydrous sodium sulfate. The solvent was then removed to obtain a residue. To this residue, a 3 mol/L ethyl acetate solution of hydrogen chloride (1 mL) was added and the mixture was stirred at room temperature for 1 hour. The solvent was again removed to obtain a residue. To this residue, ethyl acetate was added and the mixture was washed with a saturated aqueous solution of sodium hydrogen carbonate, followed by drying on anhydrous sodium sulfate. The solvent was then removed and the resulting residue was purified on a silica gel column chromatography (ethyl acetate:methanol=3:1) to obtain 9-(4-aminopiperidine-1-yl)-5-[3,5-bis(trifluoromethyl)benzyl]-6-oxo-7-phenyl-2,3,4,5-tetrahydro-6H-pyrido[2,3-b][1,5]oxazocine (35.0 mg, 78%).

MS (EI) m/z: 578 (M$^+$) HRMS (EI): Calcd for $C_{29}H_{28}F_6N_4O_2$: 578.2116; found: 578.2147. $^1$H-NMR (400 Mz, CDCl$_3$) ppm: 1.36–1.48 (2H, m), 1.59–1.88 (5H, m), 1.88–1.98 (2H, m), 2.12–2.25 (1H, m), 2.92–3.05 (2H, m), 3.27–3.36 (1H, m), 3.89 (1H, t, J=13.7 Hz), 4.09 (1H, d, J=15.1 Hz), 4.23–4.39 (2H, m), 4.45–4.52 (1H, m), 5.42 (1H, d, J=15.1 Hz), 6.37 (1H, s), 7.23–7.38 (5H, m), 7.70 (2H, s), 7.80 (1H, s)

Example 12

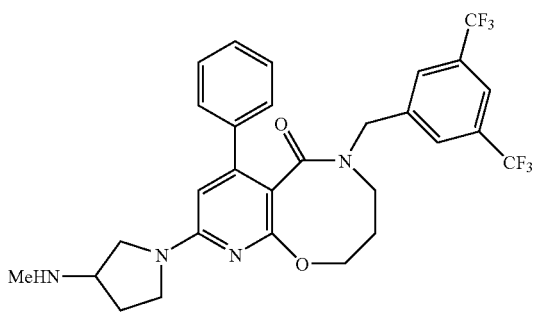

In a similar manner to Example 11, 5-[3,5-bis(trifluoromethyl)benzyl]-9-chloro-6-oxo-7-phenyl-2,3,4,5-tetrahydro- 6H-pyrido[2,3-b][1,5]oxazocine (40.0 mg) was reacted with 3-(N-(t-butoxycarbonyl)-N-methylamino)pyrrolidine (38.9 mg) to obtain 5-[3,5-bis(trifluoromethyl)benzyl]-9-[3-(methylamino)pyrrolidine-1-yl]-6-oxo-7-phenyl-2,3,4,5-tetrahydro-6H-pyrido[2,3-b][1,5]oxazocine (22.5 mg, 50%).

MS (EI) m/z: 578 (M$^+$) HRMS (EI): Calcd for $C_{29}H_{28}F_6N_4O_2$: 578.2116; found: 578.2080.

Example 13

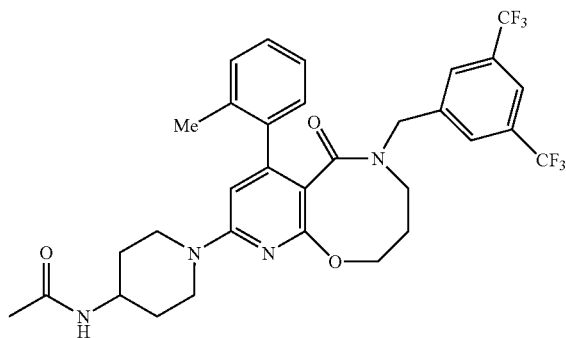

A mixture of 5-[3,5-bis(trifluoromethyl)benzyl]-9-chloro-7-(2-methylphenyl)-6-oxo-2,3,4,5-tetrahydro-6H-pyrido[2,3-b][1,5]oxazocine (47.6 mg), 4-(t-butoxycarbonylamino)piperidine (45.1 mg), and 1,4-dioxane (1 mL) was stirred at 150° C. for 3 hours. The solvent was then removed to obtain a residue. To this residue, a 3 mol/L ethyl acetate solution of hydrogen chloride (1 mL) was added and the mixture was stirred at room temperature for 1 hour. The solvent was removed and the resulting residue was dissolved in tetrahydrofuran (1 ml). While the solution was chilled on an ice bath, triethylamine (60 μl) and acetylchloride (30 μl) were added, and the mixture was stirred at room temperature for 30 min. This was followed by the addition of ethyl acetate, and the mixture was washed with water and was then dried on anhydrous sodium sulfate. Subsequently, the solvent was removed and the resulting residue was purified on a silica gel column chromatography (ethyl acetate) to obtain 9-[4-(acetylamino)piperidine-1-yl]-5-[3,5-bis(trifluoromethyl)benzyl]-7-(2-methylphenyl)-6-oxo-2,3,4,5-tetrahydro-6H-pyrido[2,3-b][1,5]oxazocine (19.2 mg, 34%).

MS (EI) m/z: 634 (M$^+$) HRMS (EI): Calcd for $C_{32}H_{32}F_6N_4O_3$: 634.2379; found: 634.2392. $^1$H-NMR (400 Mz, CDCl$_3$) ppm: 1.34–1.48 (2H, m), 1.80–1.95 (2H, m), 1.95–2.20 (6H, m), 2.31 (2H, s), 2.95–3.08 (2H, m), 3.12–3.23 (1H, m), 3.64–3.83 (1H, m), 3.90–3.98 (1H, m), 3.98–4.10 (1H, m), 4.14–4.26 (1H, m), 4.26–4.51 (3H, m), 5.31–5.43 (2H, m), 6.26 (1H, s), 6.76–7.33 (4H, m), 7.52 (2H, s), 7.76 (1H, s)

Example 14

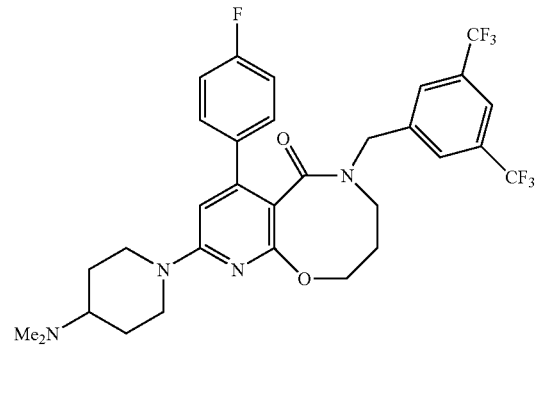

In a similar manner to Example 1, 5-[3,5-bis(trifluoromethyl)benzyl]-9-chloro-7-(4-fluorophenyl)-6-oxo-2,3,4,5-tetrahydro-6H-pyrido[2,3-b][1,5]oxazocine (53.3 mg) was reacted with 4-(dimethylamino)piperidine (15.4 mg) to obtain 5-[3,5-bis(trifluoromethyl)benzyl]-9-[4-(dimethylamino)piperidine-1-yl]-7-(4-fluorophenyl)-6-oxo-2,3,4,5-tetrahydro-6H-pyrido[2,3-b][1,5]oxazocine (22.6 mg, 36%).

MS (EI) m/z: 624 (M$^+$) HRMS (EI): Calcd for $C_{31}H_{31}F_7N_4O_2$: 624.2335; found: 624.2291.

Example 15

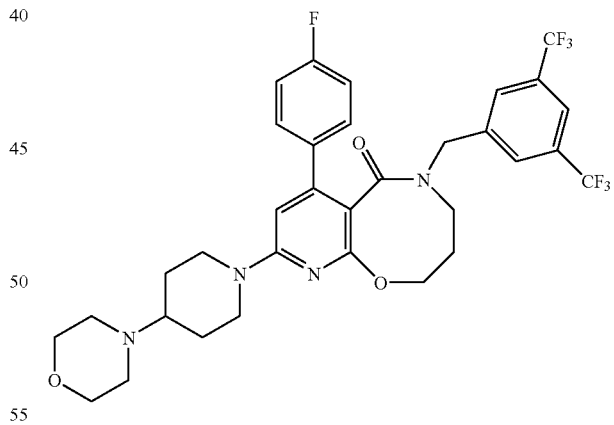

In a similar manner to Example 1, 5-[3,5-bis(trifluoromethyl)benzyl]-9-chloro-7-(4-fluorophenyl)-6-oxo-2,3,4,5-tetrahydro-6H-pyrido[2,3-b][1,5]oxazocine (53.3 mg) was reacted with 4-(morpholine-4-yl)piperidine (20.4 mg) to obtain 5-[3,5-bis(trifluoromethyl)benzyl]-7-(4-fluorophenyl)-9-[4-(morpholine-4-yl)piperidine-1-yl]-6-oxo-2,3,4,5-tetrahydro-6H-pyrido[2,3-b][1,5]oxazocine (26.2 mg, 39%).

MS (EI) m/z: 666 (M$^+$) HRMS (EI): Calcd for $C_{33}H_{33}F_7N_4O_3$: 666.2441; found: 666.2433.

Example 16

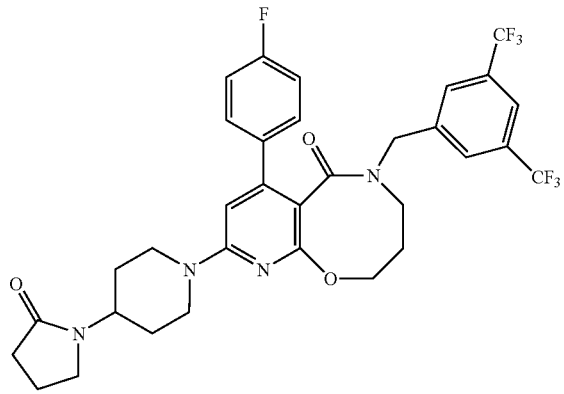

In a similar manner to Example 1, 5-[3,5-bis(trifluoromethyl)benzyl]-9-chloro-7-(4-fluorophenyl)-6-oxo-2,3,4,5-tetrahydro-6H-pyrido[2,3-b][1,5]oxazocine (53.3 mg) was reacted with 4-(2-oxopyrrolidine-1-yl)piperidine (20.2 mg) to obtain 5-[3,5-bis(trifluoromethyl)benzyl]-7-(4-fluorophenyl)-6-oxo-9-[4-(2-oxopyrrolidine-1-yl)piperidine-1-yl]-2,3,4,5-tetrahydro-6H-pyrido[2,3-b][1,5]oxazocine (26.1 mg, 39%).

MS (EI) m/z: 664 (M$^+$) HRMS (EI): Calcd for $C_{33}H_{31}F_7N_4O_3$: 664.2284; found: 664.2325.

Example 17

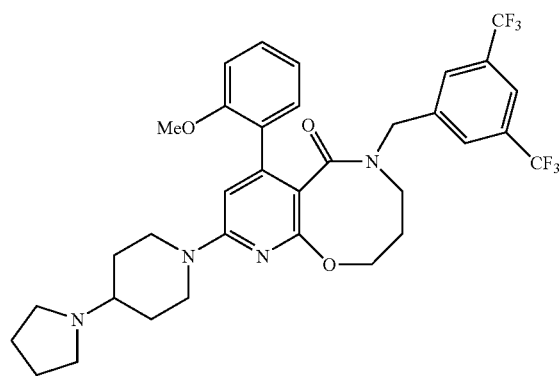

In a similar manner to Example 1, 5-[3,5-bis(trifluoromethyl)benzyl]-9-chloro-7-(2-methoxyphenyl)-6-oxo-2,3,4,5-tetrahydro-6H-pyrido[2,3-b][1,5]oxazocine (82.0 mg) was reacted with 4-(pyrrolidine-1-yl)piperidine (69.5 mg) to obtain 5-[3,5-bis(trifluoromethyl)benzyl]-7-(2-methoxyphenyl)-6-oxo-9-[4-(pyrrolidine-1-yl)piperidine-1-yl]-2,3,4,5-tetrahydro-6H-pyrido[2,3-b][1,5]oxazocine (38.4 mg, 39%).

MS (EI) m/z: 662 (M$^+$) HRMS (EI): Calcd for $C_{34}H_{36}F_6N_4O_3$: 662.2692; found: 662.2711.

Example 18

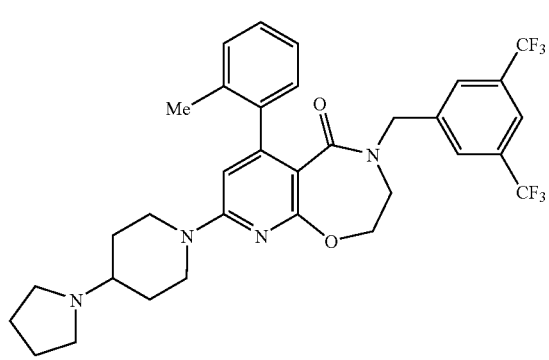

In a similar manner to Example 1, 4-[3,5-bis(trifluoromethyl)benzyl]-8-chloro-6-(2-methylphenyl)-5-oxo-2,3,4,5-tetrahydropyrido[3,2-f][1,4]oxazepine (51.5 mg) was reacted with 4-(pyrrolidine-1-yl)piperidine (46.3 mg) to obtain 4-[3,5-bis(trifluoromethyl)benzyl]-6-(2-methylphenyl)-5-oxo-8-[4-(pyrrolidine-1-yl)piperidine-1-yl]-2,3,4,5-tetrahydropyrido[3,2-f][1,4]oxazepine (8.6 mg, 14%).

MS (EI) m/z: 632 (M$^+$) HRMS (EI): Calcd for $C_{33}H_{34}F_6N_4O_2$: 632.2586; found: 632.2571.

Example 19

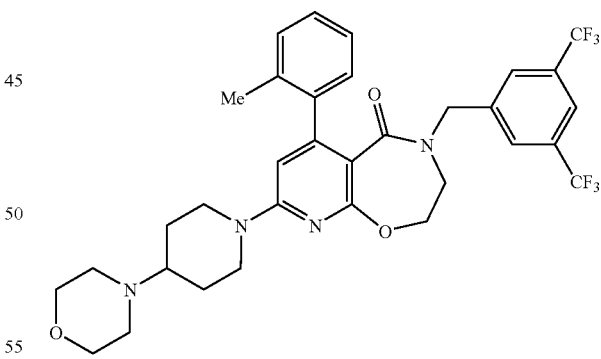

In a similar manner to Example 1, 4-[3,5-bis(trifluoromethyl)benzyl]-8-chloro-6-(2-methylphenyl)-5-oxo-2,3,4,5-tetrahydropyrido[3,2-f][1,4]oxazepine (51.5 mg) was reacted with 4-(morpholine-4-yl)piperidine (51.1 mg) to obtain 4-[3,5-bis(trifluoromethyl)benzyl]-6-(2-methylphenyl)-8-[4-(morpholine-4-yl)piperidine-1-yl]-5-oxo-2,3,4,5-tetrahydropyrido[3,2-f][1,4]oxazepine (8.3 mg, 13%).

MS (EI) m/z: 648 (M$^+$) HRMS (EI): Calcd for $C_{33}H_{34}F_6N_4O_3$: 648.2535; found: 648.2526.

Example 20

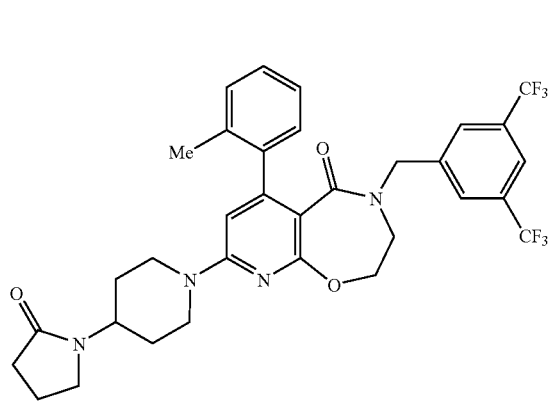

In a similar manner to Example 1, 4-[3,5-bis(trifluoromethyl)benzyl]-8-chloro-6-(2-methylphenyl)-5-oxo-2,3,4,5-tetrahydropyrido[3,2-f][1,4]oxazepine (51.5 mg) was reacted with 4-(2-oxopyrrolidine-1-yl)piperidine (50.5 mg) to obtain 4-[3,5-bis(trifluoromethyl)benzyl]-6-(2-methylphenyl)-8-[4-(2-oxopyrrolidine-1-yl)piperidine-1-yl]-5-oxo-2,3,4,5-tetrahydropyrido[3,2-f][1,4]oxazepine (5.2 mg, 8%).

MS (EI) m/z: 646 (M⁺) HRMS (EI): Calcd for $C_{33}H_{32}F_6N_4O_3$: 646.2379; found: 646.2352.

Example 21

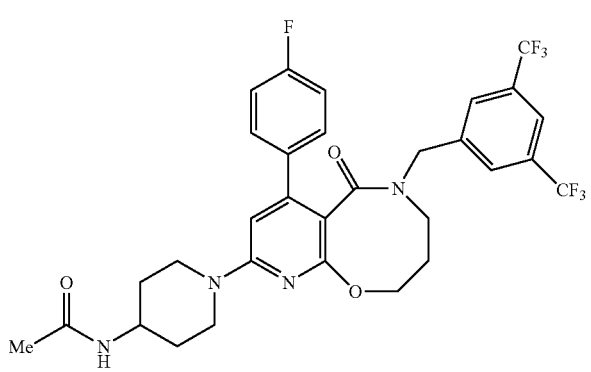

In a similar manner to Example 13, 5-[3,5-bis(trifluoromethyl)benzyl]-9-chloro-7-(4-fluorophenyl)-6-oxo-2,3,4,5-tetrahydro-6H-pyrido[2,3-b][1,5]oxazocine (53.3 mg) was reacted with 4-(t-butoxycarbonylamino)piperidine (24.0 mg) to obtain 9-[4-(acetylamino)piperidine-1-yl]-5-[3,5-bis(trifluoromethyl)benzyl]-7-(4-fluorophenyl)-6-oxo-2,3,4,5-tetrahydro-6H-pyrido[2,3-b][1,5]oxazocine (13.7 mg, 21%).

MS (EI) m/z: 638 (M⁺) HRMS (EI): Calcd for $C_{31}H_{29}F_7N_4O_3$: 638.2128; found: 638.2155.

Example 22

In a similar manner to Example 13, 5-[3,5-bis(trifluoromethyl)benzyl]-9-chloro-7-(4-fluorophenyl)-6-oxo-2,3,4,5-tetrahydro-6H-pyrido[2,3-b][1,5]oxazocine (53.3 mg) was reacted with 4-(t-butoxycarbonylamino)piperidine (24.0 mg) to obtain 9-[4-(methylsulfonylamino)piperidine-1-yl]-5-[3,5-bis(trifluoromethyl)benzyl]-7-(4-fluorophenyl)-6-oxo-2,3,4,5-tetrahydro-6H-pyrido[2,3-b][1,5]oxazocine (20.4 mg, 30%).

MS (EI) m/z: 674 (M⁺) HRMS (EI): Calcd for $C_{30}H_{29}F_7N_4O_4S$: 674.1798; found: 674.1806.

Reference Example 1

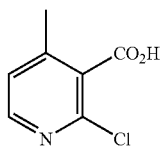

To a tetrahydrofuran solution of lithium diisopropylamide (which was prepared by diluting diisopropylamine (14.6 mL) with tetrahydrofuran (200 mL), followed by addition of n-butyllithium (69.5 mL, 1.5 mol/L hexane solution) at −20° C. and then a 30-minute stirring period at −20° C.), a tetrahydrofuran solution (100 mL) of 2-chloro-3-iodopyridine (23.8 g) was added at −78° C. and the mixture was stirred for 5 hours. Carbon dioxide was then bubbled through the reaction mixture for 1 hour and water was added. The temperature of the mixture was then allowed to rise to room temperature. Following the addition of 2 mol/L hydrochloric acid (200 mL) to adjust the pH of the mixture to a value of 1, the mixture was extracted with a 1:1 mixture of tetrahydrofuran and ethyl acetate and was dried on anhydrous sodium sulfate. The solvent was then removed to obtain a residue. To this residue, ethyl acetate was added and the resultant crystals were collected by filtration. As a result, 2-chloro-4-iodonicotinic acid was obtained (22.7 g, 81%).

MS (EI) m/z: 283 (M⁺) HRMS (EI): Calcd for $C_6H_3ClINO_2$: 282.8897; found: 282.8896.

Reference Example 2

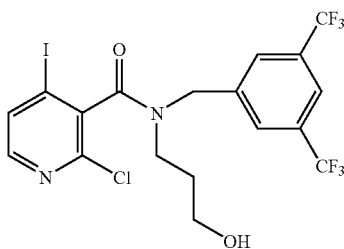

To thionyl chloride (20 mL), 2-chloro-4-iodonicotinic acid (8.40 g) were added along with N,N-dimethylformamide (3 droplets) and the mixture was stirred at 100° C. for 3 hours. The reaction mixture was then distilled under reduced pressure to obtain a yellow residue. 3-(3,5-bis (trifluoromethyl)benzylamino)propanol (10.7 g) and triethylamine (20.6 mL) were dissolved in tetrahydrofuran (150 mL). While the mixture was chilled on an ice bath, a tetrahydrofuran solution of the yellow residue (50 mL) was added. After stirred for 1 hour, the mixture was further stirred for additional two hours at room temperature. Subsequently, water was added to the reaction mixture and the mixture was extracted with ethyl acetate. The extract was then dried on anhydrous sodium sulfate. Following the removal of the solvent, the remaining residue was purified on a silica gel column chromatography (ethyl acetate:n-hexane=3:1) to obtain N-[3,5-bis(trifluoromethyl)benzyl]-2-chloro-N-(3-hydroxypropyl)-4-iodonicotinamide (15.4 g, 92%).

MS (EI) m/z: 566 (M$^+$) HRMS (EI): Calcd for $C_{18}H_{14}ClF_6N_2O_2$: 565.9693; found: 565.9731.

Reference Example 3

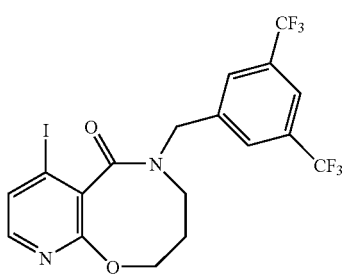

N-[3,5-bis(trifluoromethyl)benzyl]-2-chloro-N-(3-hydroxypropyl)-4-iodonicotinamide (6.86 g) was dissolved in tetrahydrofuran (60 mL). While the mixture was chilled on an ice bath, sodium hydride (581 mg, 60% oil suspension) was added and the mixture was stirred for 30 min. Subsequently, the temperature of the mixture was allowed to rise to room temperature and the mixture was stirred for another hour. While the mixture was chilled on an ice bath, water was added and the resulting mixture was extracted with ethyl acetate. The extract was washed with a saturated aqueous solution of sodium chloride and was then dried on anhydrous sodium sulfate. The solvent was removed and the resulting residue was purified on a silica gel column chromatography (ethyl acetate:n-hexane=2:1) to obtain 5-[3,5-bis(trifluoromethyl)benzyl]-7-iodo-6-oxo-2,3,4,5-tetrahydro-6H-pyrido[2,3-b][1,5]oxazocine (2.69 g, 42%).

MS (EI) m/z: 530 (M$^+$) HRMS (EI): Calcd for $C_{18}H_{13}F_6IN_2O_2$: 529.9926; found: 529.9907.

Reference Example 4

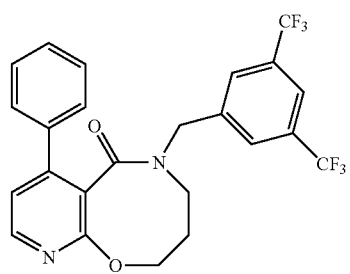

Phenylboronic acid (417 mg), tetrakis(triphenylphosphine)palladium (132 mg), toluene (10 mL), 1,4-dioxane (5 mL), and a 2 mol/L aqueous solution of sodium carbonate (10 mL) were added to 5-[3,5-bis(trifluoromethyl)benzyl]-7-iodo-6-oxo-2,3,4,5-tetrahydro-6H-pyrido[2,3-b][1,5]oxazocine (1.00 g). While heated, the mixture was stirred for 7 hours under a stream of argon gas. The mixture was then diluted with ethyl acetate, was washed with a 2 mol/L aqueous solution of sodium carbonate, and was dried on anhydrous sodium sulfate. The solvent was removed and the resulting residue was recrystallized from isopropanol to obtain 5-[3,5-bis(trifluoromethyl)benzyl]-6-oxo-7-phenyl-2,3,4,5-tetrahydro-6H-pyrido[2,3-b][1,5]oxazocine (729 mg, 80%).

MS (EI) m/z: 480 (M$^+$) HRMS (EI): Calcd for $C_{24}H_{18}F_6N_2O_2$: 480.1272; found: 480.1286.

Reference Example 5

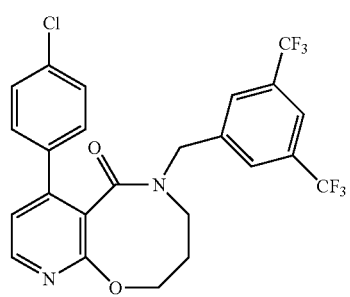

In a similar manner to Reference Example 4, 5-[3,5-bis(trifluoromethyl)benzyl]-7-iodo-6-oxo-2,3,4,5-tetrahydro-6H-pyrido[2,3-b][1,5]oxazocine (300 mg) was reacted with 4-chlorophenylboronic acid (160 mg) to obtain 5-[3,5-bis(trifluoromethyl)benzyl]-7-(4-chlorophenyl)-6-oxo-2,3,4,5-tetrahydro-6H-pyrido[2,3-b][1,5]oxazocine (292 mg, 100%).

MS (EI) m/z: 514 (M$^+$) HRMS (EI): Calcd for $C_{24}H_{17}ClF_6N_2O_2$: 514.0883; found: 514.0878.

Reference Example 6

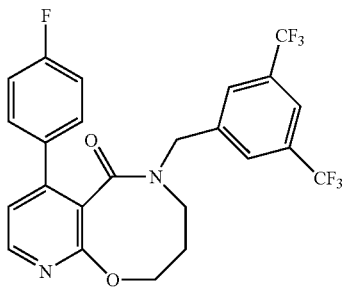

In a similar manner to Reference Example 4, 5-[3,5-bis(trifluoromethyl)benzyl]-7-iodo-6-oxo-2,3,4,5-tetrahydro-6H-pyrido[2,3-b][1,5]oxazocine (300 mg) was reacted with 4-fluorophenylboronic acid (143 mg) to obtain 5-[3,5-bis(trifluoromethyl)benzyl]-7-(4-fluorophenyl)-6-oxo-2,3,4,5-tetrahydro-6H-pyrido[2,3-b][1,5]oxazocine (284 mg, 100%).

MS (EI) m/z: 498 (M$^+$) HRMS (EI): Calcd for $C_{24}H_{17}F_7N_2O_2$: 498.1178; found: 498.1168.

Reference Example 7

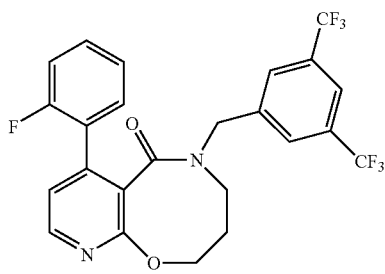

In a similar manner to Reference Example 4, 5-[3,5-bis(trifluoromethyl)benzyl]-7-iodo-6-oxo-2,3,4,5-tetrahydro-6H-pyrido[2,3-b][1,5]oxazocine (300 mg) was reacted with 2-fluorophenylboronic acid (143 mg) to obtain 5-[3,5-bis(trifluoromethyl)benzyl]-7-(2-fluorophenyl)-6-oxo-2,3,4,5-tetrahydro-6H-pyrido[2,3-b][1,5]oxazocine (218 mg, 77%).

MS (EI) m/z: 498 (M$^+$) HRMS (EI): Calcd for $C_{24}H_{17}F_7N_2O_2$: 498.1178; found: 498.1168.

Reference Example 8

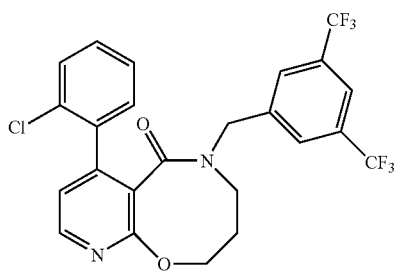

In a similar manner to Reference Example 4, 5-[3,5-bis(trifluoromethyl)benzyl]-7-iodo-6-oxo-2,3,4,5-tetrahydro-6H-pyrido[2,3-b][1,5]oxazocine (300 mg) was reacted with 2-chlorophenylboronic acid (133 mg) to obtain 5-[3,5-bis(trifluoromethyl)benzyl]-7-(2-chlorophenyl)-6-oxo-2,3,4,5-tetrahydro-6H-pyrido[2,3-b][1,5]oxazocine (254 mg, 87%).

MS (FAB$^+$) m/z: 515 (M+H$^+$) HRMS (FAB$^+$): Calcd for $C_{24}H_{18}ClF_6N_2O_2$: 515.0961; found: 515.0932.

Reference Example 9

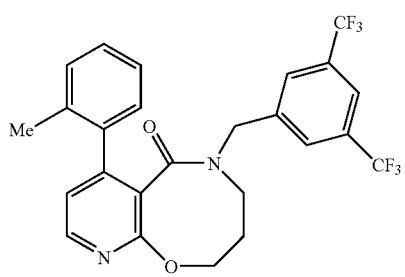

In a similar manner to Reference Example 4, 5-[3,5-bis(trifluoromethyl)benzyl]-7-iodo-6-oxo-2,3,4,5-tetrahydro-6H-pyrido[2,3-b][1,5]oxazocine (300 mg) was reacted with 2-methylphenylboronic acid (116 mg) to obtain 5-[3,5-bis(trifluoromethyl)benzyl]-7-(2-methylphenyl)-6-oxo-2,3,4,5-tetrahydro-6H-pyrido[2,3-b][1,5]oxazocine (278 mg, 99%).

MS (EI) m/z: 494 (M$^+$) HRMS (EI): Calcd for $C_{25}H_{20}F_6N_2O_2$: 494.1429; found: 494.1441.

Reference Example 10

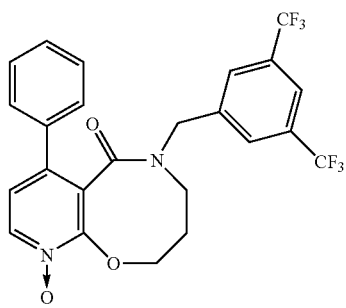

5-[3,5-bis(trifluoromethyl)benzyl]-6-oxo-7-phenyl-2,3,4,5-tetrahydro-6H-pyrido[2,3-b][1,5]oxazocine (729 mg) was dissolved in methylene chloride (10 mL) and 3-chloroperbenzoic acid (524 mg) was added to the solution. The resulting mixture was then stirred at room temperature for 24 hours. The reaction mixture was purified on a silica gel column chromatography (ethyl acetate:methanol=5:1) to obtain 5-[3,5-bis(trifluoromethyl)benzyl]-6-oxo-7-phenyl-2,3,4,5-tetrahydro-6H-pyrido[2,3-b][1,5]oxazocine 10-oxide (411 mg, 54%).

MS (FAB$^+$) m/z: 497 (M+H$^+$) HRMS (FAB$^+$): Calcd for $C_{24}H_{19}F_6N_2O_3$: 497.1300; found: 497.1291.

Reference Example 11

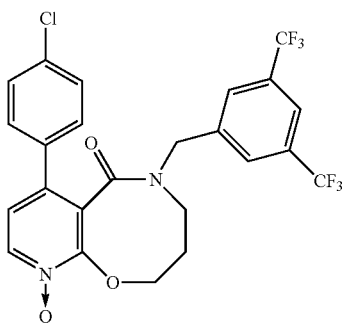

In a similar manner to Reference Example 10, 5-[3,5-bis(trifluoromethyl)benzyl]-7-(4-chlorophenyl)-6-oxo-2,3,4,5-tetrahydro-6H-pyrido[2,3-b][1,5]oxazocine (290 mg) was used to obtain 5-[3,5-bis(trifluoromethyl)benzyl]-7-(4-chlorophenyl)-6-oxo-2,3,4,5-tetrahydro-6H-pyrido[2,3-b][1,5]oxazocine 10-oxide (112 mg, 37%).

MS (FAB$^+$) m/z: 531 (M+H$^+$) HRMS (FAB$^+$): Calcd for $C_{24}H_{18}ClF_6N_2O_3$: 531.0910; found: 531.0892.

Reference Example 12

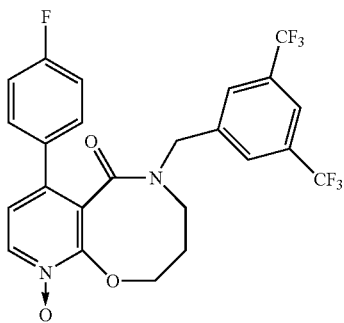

In a similar manner to Reference Example 10, 5-[3,5-bis(trifluoromethyl)benzyl]-7-(4-fluorophenyl)-6-oxo-2,3,4,5-tetrahydro-6H-pyrido[2,3-b][1,5]oxazocine (272 mg) was used to obtain 5-[3,5-bis(trifluoromethyl)benzyl]-7-(4-fluorophenyl)-6-oxo-2,3,4,5-tetrahydro-6H-pyrido[2,3-b][1,5]oxazocine 10-oxide (119 mg, 42%).

MS (FAB$^+$) m/z: 515 (M+H$^+$) HRMS (FAB$^+$): Calcd for $C_{24}H_{18}F_7N_2O_3$: 515.1206; found: 515.1230.

Reference Example 13

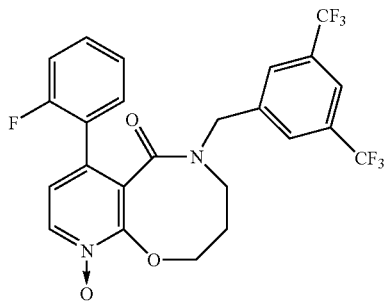

In a similar manner to Reference Example 10, 5-[3,5-bis(trifluoromethyl)benzyl]-7-(2-fluorophenyl)-6-oxo-2,3,4,5-tetrahydro-6H-pyrido[2,3-b][1,5]oxazocine (238 mg) was use to obtain 5-[3,5-bis(trifluoromethyl)benzyl]-7-(2-fluorophenyl)-6-oxo-2,3,4,5-tetrahydro-6H-pyrido[2,3-b][1,5]oxazocine 10-oxide (178 mg, 72%).

MS (FAB$^+$) m/z: 515 (M+H$^+$) HRMS (FAB$^+$): Calcd for $C_{24}H_{18}F_7N_2O_3$: 515.1206; found: 515.1189.

Reference Example 14

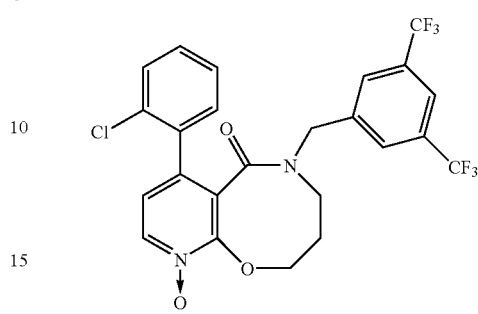

In a similar manner to Reference Example 10, 5-[3,5-bis(trifluoromethyl)benzyl]-7-(2-chlorophenyl)-6-oxo-2,3,4,5-tetrahydro-6H-pyrido[2,3-b][1,5]oxazocine (250 mg) was used to obtain 5-[3,5-bis(trifluoromethyl)benzyl]-7-(2-chlorophenyl)-6-oxo-2,3,4,5-tetrahydro-6H-pyrido[2,3-b][1,5]oxazocine 10-oxide (207 mg, 80%).

MS (FAB$^+$) m/z: 531 (M+H$^+$) HRMS (FAB$^+$): Calcd for $C_{24}H_{18}ClF_6N_2O_3$: 531.0910; found: 531.0877.

Reference Example 15

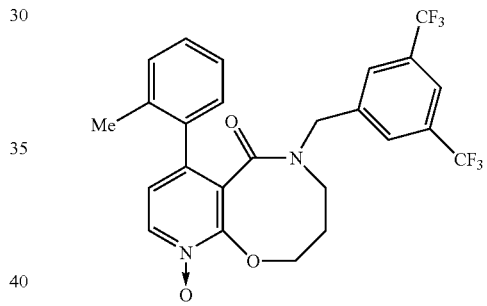

In a similar manner to Reference Example 10, 5-[3,5-bis(trifluoromethyl)benzyl]-7-(2-methylphenyl)-6-oxo-2,3,4,5-tetrahydro-6H-pyrido[2,3-b][1,5]oxazocine (270 mg) was used to obtain 5-[3,5-bis(trifluoromethyl)benzyl]-7-(2-methylphenyl)-6-oxo-2,3,4,5-tetrahydro-6H-pyrido[2,3-b][1,5]oxazocine 10-oxide (231 mg, 83%).

MS (FAB$^+$) m/z: 511 (M+H$^+$) HRMS (FAB$^+$): Calcd for $C_{25}H_{21}F_6N_2O_3$: 511.1456; found: 511.1469.

Reference Example 16

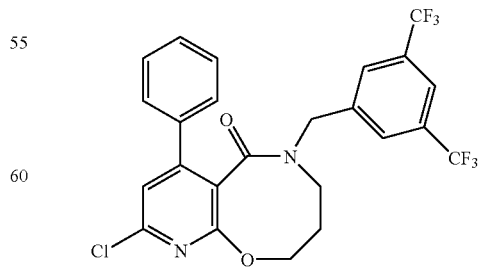

5-[3,5-bis(trifluoromethyl)benzyl]-6-oxo-7-phenyl-2,3,4,5-tetrahydro-6H-pyrido[2,3-b][1,5]oxazocine 10-oxide (400 mg) was added to phosphorus oxychloride (1.5 mL), and the mixture was refluxed for 1 hour while heated.

The solvent was removed to obtain a residue. To this residue, ethyl acetate was added and the resulting crystals were collected. As a result, 5-[3,5-bis(trifluoromethyl)benzyl]-9-chloro-6-oxo-7-phenyl-2,3,4,5-tetrahydro-6H-pyrido[2,3-b][1,5]oxazocine was obtained (440 mg, 99%).

MS (EI) m/z: 514 (M+) HRMS (EI): Calcd for $C_{24}H_{17}ClF_6N_2O_2$: 514.0883; found: 514.0865.

Reference Example 17

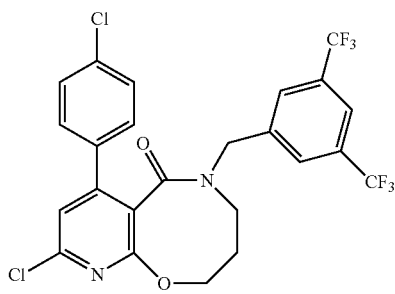

In a similar manner to Reference Example 16, 5-[3,5-bis(trifluoromethyl)benzyl]-7-(4-chlorophenyl)-6-oxo-2,3,4,5-tetrahydro-6H-pyrido[2,3-b][1,5]oxazocine 10-oxide (107 mg) was used to obtain 5-[3,5-bis(trifluoromethyl)benzyl]-9-chloro-7-(4-chlorophenyl)-6-oxo-2,3,4,5-tetrahydro-6H-pyrido[2,3-b][1,5]oxazocine (111 mg, 100%).

MS (EI) m/z: 548 (M+) HRMS (EI): Calcd for $C_{24}H_{16}Cl_2F_6N_2O_2$: 548.0493; found: 548.0508.

Reference Example 18

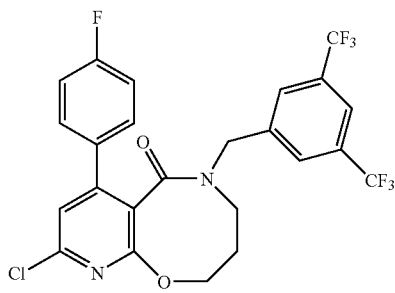

In a similar manner to Reference Example 16, 5-[3,5-bis(trifluoromethyl)benzyl]-7-(4-fluorophenyl)-6-oxo-2,3,4,5-tetrahydro-6H-pyrido[2,3-b][1,5]oxazocine 10-oxide (114 mg) was used to obtain 5-[3,5-bis(trifluoromethyl)benzyl]-9-chloro-7-(4-fluorophenyl)-6-oxo-2,3,4,5-tetrahydro-6H-pyrido[2,3-b][1,5]oxazocine (118 mg, 100%).

MS (EI) m/z: 532 (M+) HRMS (EI): Calcd for $C_{24}H_{16}ClF_7N_2O_2$: 532.0798; found: 532.0801.

Reference Example 19

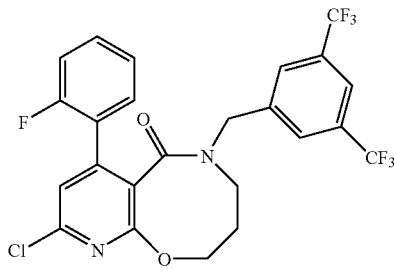

In a similar manner to Reference Example 16, 5-[3,5-bis(trifluoromethyl)benzyl]-7-(2-fluorophenyl)-6-oxo-2,3,4,5-tetrahydro-6H-pyrido[2,3-b][1,5]oxazocine 10-oxide (170 mg) was used to obtain 5-[3,5-bis(trifluoromethyl)benzyl]-9-chloro-7-(2-fluorophenyl)-6-oxo-2,3,4,5-tetrahydro-6H-pyrido[2,3-b][1,5]oxazocine (176 mg, 100%).

MS (EI) m/z: 532 (M+) HRMS (EI): Calcd for $C_{24}H_{16}ClF_7N_2O_2$: 532.0789; found: 532.0824.

Reference Example 20

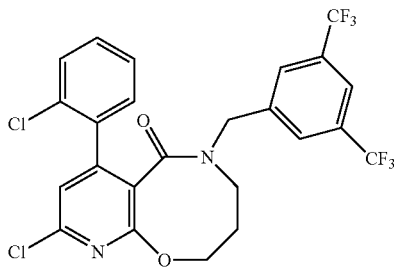

In a similar manner to Reference Example 16, 5-[3,5-bis(trifluoromethyl)benzyl]-7-(2-chlorophenyl)-6-dioxo-2,3,4,5-tetrahydro-6H-pyrido[2,3-b][1,5]oxazocine 10-oxide (196 mg) was used to obtain 5-[3,5-bis(trifluoromethyl)benzyl]-9-chloro-7-(2-chlorophenyl)-6-oxo-2,3,4,5-tetrahydro-6H-pyrido[2,3-b][1,5]oxazocine (203 mg, 100%).

MS (FAB+) m/z: 549 (M+H+) HRMS (FAB+): Calcd for $C_{24}H_{17}Cl_2F_6N_2O_2$: 549.0571; found: 549.0605.

Reference Example 21

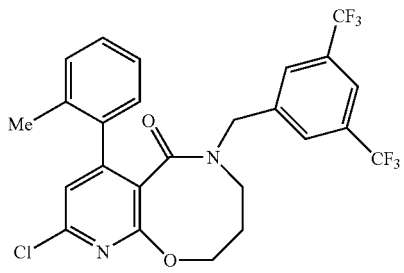

In a similar manner to Reference Example 16, 5-[3,5-bis(trifluoromethyl)benzyl]-7-(2-methylphenyl)-6-oxo-2,3,4, 5-tetrahydro-6H-pyrido[2,3-b][1,5]oxazocine 10-oxide (220 mg) was used to obtain 5-[3,5-bis(trifluoromethyl)benzyl]-9-chloro-7-(2-methylphenyl)-6-oxo-2,3,4,5-tetrahydro-6H-pyrido[2,3-b][1,5]oxazocine (228 mg, 100%).

MS (EI) m/z: 528 (M$^+$) HRMS (EI): Calcd for $C_{25}H_{19}ClF_6N_2O_2$: 528.1039; found: 528.1063.

Reference Example 22

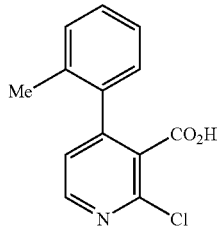

In a similar manner to Reference Example 4, 2-chloro-4-iodonicotinic acid (Compound of Reference Example 1; 5.67 g) was reacted with 2-methylphenylboronic acid (3.00 g) to obtain 2-chloro-4-(2-methylphenyl)nicotinic acid (4.44 g, 90%).

MS (EI) m/z: 247 (M$^+$) HRMS (EI): Calcd for $C_{13}H_{10}ClNO_2$: 247.0400; found: 247.0410.

Reference Example 23

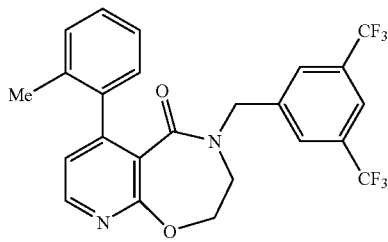

2-chloro-4-(2-methylphenyl)nicotinic acid (Compound of Reference Example 22; 670 mg) and N,N-dimethylformamide (2 droplets) were added to thionyl chloride (2.0 mL). While heated, the mixture was refluxed for 1 hour. The reaction mixture was distilled under reduced pressure to obtain a colorless residue.

3-(3,5-bis(trifluoromethyl)benzylamino)propanol (Prepared according to a method described in Japanese Patent Laid-Open Publication No. Hei 9-263585; 818 mg) and triethylamine (1.9 mL) were dissolved in tetrahydrofuran (8 mL). While this solution was chilled on an ice bath, the yellow residue in tetrahydrofuran (2 mL) was added. After stirred for 1 hour, the mixture was further stirred for an additional 1 hour at room temperature. Subsequently, the mixture was diluted with ethyl acetate. The diluted mixture was successively washed with water, a saturated aqueous solution of sodium hydrogen carbonate, a 20% aqueous citric acid, and a saturated aqueous solution of sodium chloride, and was then dried on anhydrous sodium sulfate. The solvent was removed and the resulting residue was dissolved in tetrahydrofuran (8 mL). While this solution was chilled on an ice bath, potassium-t-butoxide (365 mg) was added. After stirred for 1 hour, the mixture was further stirred for an additional 1 hour at room temperature. Following dilution with ethyl acetate, the mixture was successively washed with water and a saturated aqueous solution of sodium chloride and was then dried on anhydrous sodium sulfate. The solvent was removed and the resulting residue was purified on a silica gel column chromatography (ethyl acetate:n-hexane=2:1) to obtain 4-[3,5-bis(trifluoromethyl)benzyl]-6-(2-methylphenyl)-5-oxo-2,3,4,5-tetrahydropyrido[3,2-f][1,4]oxazepine (590 mg, 45%).

MS (EI) m/z: 480 (M$^+$) HRMS (EI): Calcd for $C_{24}H_{18}F_6N_2O_2$: 480.1272; found: 480.1293.

Reference Example 24

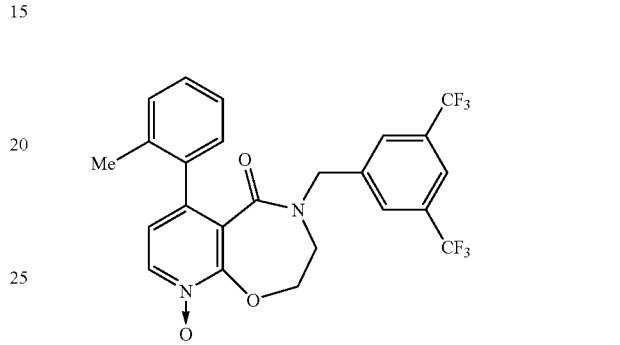

In a similar manner to Reference Example 10, 4-[3,5-bis(trifluoromethyl)benzyl]-6-(2-methylphenyl)-5-oxo-2,3,4,5-tetrahydropyrido[3,2-f][1,4]oxazepine (Compound of Reference Example 23; 530 mg) was used to obtain 4-[3,5-bis(trifluoromethyl)benzyl]-6-(2-methylphenyl)-5-oxo-2,3,4,5-tetrahydropyrido[3,2-f][1,4]oxazepine 10-oxide (333 mg, 61%).

MS (FAB$^+$) m/z: 497 (M+H$^+$) HRMS (FAB$^+$): Calcd for $C_{24}H_{19}F_6N_2O_3$: 497.1300; found: 497.1311.

Reference Example 25

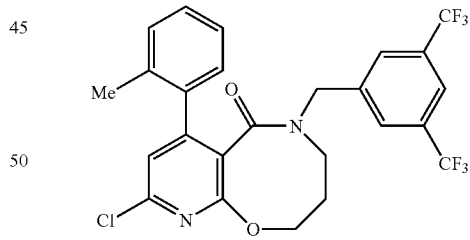

In a similar manner to Reference Example 16, 4-[3,5-bis(trifluoromethyl)benzyl]-6-(2-methylphenyl)-5-oxo-2,3,4,5-tetrahydropyrido[3,2-f][1,4]oxazepine 10-oxide (Compound of Reference Example 24; 310 mg) was used to obtain 4-[3,5-bis(trifluoromethyl)benzyl]-8-chloro-6-(2-methylphenyl)-5-oxo-2,3,4,5-tetrahydropyrido[3,2-f][1,4]oxazepine 10-oxide (320 mg, 100%).

MS (EI) m/z: 514 (M$^+$) HRMS (EI): Calcd for $C_{24}H_{17}ClF_6N_2O_2$: 514.0883; found: 514.0840.

Evidence of the effectiveness of the compounds of the present invention is provided below with reference to Test Examples.

Test Examples (1) Test for NK1 Receptor Antagonist

The method used was according to the method proposed by S. Dion et al. (Dion et al., *Life Sciences* 41 (1987): 2269), to which minor modifications were made.

Guinea pigs were stunned by a blow on the head and were exsanguinated from the carotid artery and ileum was isolated. The ileum was mounted in an organ bath containing Tyrode's solution which was maintained at 32° C. and gased with 95% $O_2$ and 5% $CO_2$. The ileum was subjected to a resting tension of 1-gram and allowed to equilibrate for 20 minutes before the experiment was started. As a control, a concentration-response curve for substance P obtained in the absence of test compounds was used. The NK1 receptor antagonist activity of each test compound was determined by a concentration-response curve obtained by pretreating at least three concentrations of the test compound for 10 minutes and subsequently applying substance P in a cumulative manner. The Kb values were determined according to the method proposed by Schild and the results are shown in Table 1 (Schild *Brit. J. Pharmacol.* 14 (1959): 49).

The composition of the Tyrode's solution was as follows: NaCl=136.9, KCl=2.7, $CaCl_2.2H_2O$=2.5, $MgCl_2.6H_2O$=1.0, $NaH_2PO_4.2H_2O$=0.4, $NaHCO_3$=11.9, glucose=11.1 (mmol/L)

TABLE 1

| Example | Kb(nmol/L) |
|---------|------------|
| 1 | 0.224 |
| 4 | 0.148 |
| 7 | 0.210 |
| 8 | 0.275 |
| 9 | 0.0848 |
| 10 | 0.286 |
| 13 | 0.170 |

As can be seen from the results of Table 1, the compounds (1) or salts thereof according to the invention prove to be effective NK1 receptor antagonists.

(2) Cystometry Test on Guinea Pigs

The method used was according to the method proposed by J S. Peterson et al. (Peterson J S. et al., *J. Pharmacol. Methods* 21 (1989): 231), to which minor modifications were made.

Guinea pigs were anesthetized with halothane and the tenth thoracic spinal cord was cut in each animal. Subsequently, both ureters were ligated and were cut on the kidney-side. Polyethylene catheters were inserted into the bladder to provide an injection pathway for physiological saline and a pathway for the measurement of intravesical pressure. Each animal was restricted in a Ballman cage and was left for more than 2 hours. Subsequently, room-temperature saline was injected through the bladder catheter into the bladder at a rate of 6 mL/hr to conduct a cystometry test. After the effective bladder capacity was stabilized, a test compound was intravenously administered from the jugular vein. The effective bladder capacity is defined as the volume of saline injected from one urination to the next. The effect of each test compound was determined as the increase in the average bladder volume, which was determined by taking difference between the average bladder volume measured 30 minutes prior to the administration of the test compound and the average bladder volume measured every 30 minutes after the administration of the test compound. The results are shown in Table 2.

TABLE 2

| Test compounds | Dose (i.v.) mg/kg | Increase in bladder capacity (%) |
|---------|---------|---------|
| Compound of Example 7 | 0.3 | 24.2 |
| | 1 | 46.0 |
| TAK-637* | 0.3 | 12.0 |
| | 1 | 23.8 |
| | 3 | 20.5 |

*Compound described in Example 18 in Japanese Patent Laid-Open Publication No. Hei 9-263585

As can be inferred from the results of Table 2, the compounds (1) or salts thereof according to the invention have a better ability to increase the effective bladder capacity than TAK-637 in terms of their potency as well as their maximum effects.

INDUSTRIAL APPLICABILITY

As set forth, the present invention has been devised based on the discovery that the novel fused bicyclic pyridine derivatives and salts thereof act as effective tachykinin receptor antagonists.

In particular, not only have the compounds of the present invention proven to act as NK1 receptor antagonists, but they have also been shown, by the Test Examples above, to have better effects than the conventional compounds.

Specifically, when the compounds of the present invention were tested for their effects on dysuria, a tachykinin-mediated disorder, by cystometry, in which the ability of each of the compounds to increase the effective bladder capacity was measured in guinea pigs with broken spinal cords, they proved to have significantly higher pharmacological effects as compared to TAK-637, a known compound. In brief, when given in smaller doses, the compounds of the present invention exhibited pharmacological effects comparable to the conventional. TAK-637 compound. Also, the same doses of the compounds of the present invention brought about significantly better pharmacological effects and elicited higher maximum effects than TAK-637.

In addition, the compounds of the present invention and salts thereof exhibit little toxicity and are thus highly safe. Accordingly, the compounds of the present invention and salts thereof, which are effective tachykinin antagonists, are of significant usefulness in the treatment of various pathological conditions including pollakiuria.

The invention claimed is:

1. A compound of formula (1), or a salt thereof:

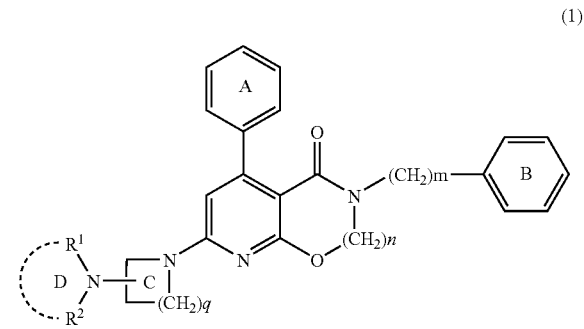

(1)

wherein the rings A and B are each a benzene ring which may have 1 to 3 substituents (any adjacent two of which may be bound to one another to form a ring selected from the group consisting of

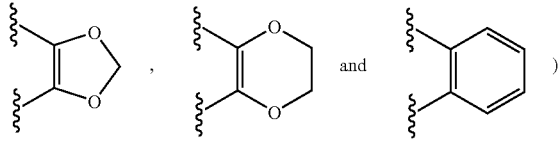

that are each independently selected from the group consisting of a halogen atom, an unsubstituted $C_1$ to $C_6$ alkyl group, a halogen-substituted $C_1$ to $C_6$ alkyl group, an unsubstituted $C_1$ to $C_6$ alkoxy group and a halogen-substituted $C_1$ to $C_6$ alkoxy group;

$R^1$ and $R^2$ are each independently a hydrogen atom, a $C_1$ to $C_6$ alkyl group, a $C_1$ to $C_6$ alkylsulfonyl group, a $C_1$ to $C_6$ alkylcarbonyl group, or a $C_1$ to $C_6$ alkoxycarbonyl group, or $R^1$ and $R^2$ are bound to one another to form the ring D, which is a 3- to 7-membered non-aromatic heterocyclic ring that may contain, aside from the nitrogen atom, 1 to 3 heteroatoms selected from the group consisting of a nitrogen atom, a sulfur atom, and an oxygen atom and may further contain 1 or 2 oxo group-substituted carbon atoms;

m is 1 or 2; n is 2 or 3; and q is an integer from 1 to 4.

2. A compound of formula (1a), or a salt thereof:

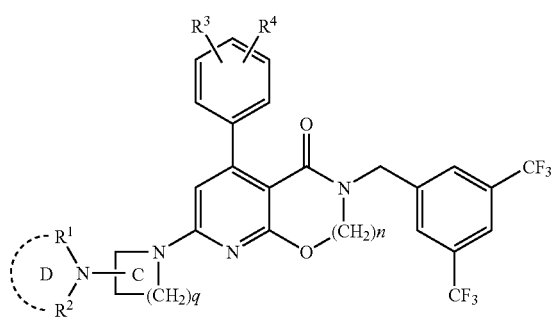

(1a)

wherein $R^3$ and $R^4$ are each independently a hydrogen atom, a fluorine atom, a chlorine atom, a methyl group, an ethyl group, a trifluoromethyl group, a methoxy group, or a trifluoromethoxy group;

$R^1$ and $R^2$ are each independently a hydrogen atom, a $C_1$ to $C_6$ alkyl group, a $C_1$ to $C_6$ alkylsulfonyl group, a $C_1$ to $C_6$ alkylcarbonyl group, or a $C_1$ to $C_6$ alkoxycarbonyl group, or $R^1$ and $R^2$ are bound to one another to form the ring D, which is a 3- to 7-membered non-aromatic heterocyclic ring that may contain, aside from the nitrogen atom, 1 to 3 heteroatoms selected from the group consisting of a nitrogen atom, a sulfur atom, and an oxygen atom and may further contain 1 or 2 oxo group-substituted carbon atoms;

n is 2 or 3; and q is an integer from 1 to 4.

3. The compound according to claim 2 or a salt thereof, wherein in the formula (1a), n is 3.

4. The compound according to claim 2 or a salt thereof, wherein in the formula (1a), n is 3, and q in the ring C is 3.

5. The compound according to claim 2 or a salt thereof, wherein in the formula (1a), n is 3, q in the ring C is 3, and the ring D is represented by the following formula:

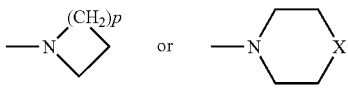

wherein p is an integer from 1 to 4, and X is an oxygen atom, a nitrogen atom, or a sulfur atom.

6. The compound according to claim 2 or a salt thereof, wherein in the formula (1a), n is 3, q in the ring C is 3, and the ring D is represented by the following formula:

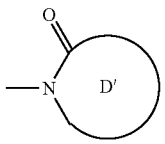

wherein the ring D' is a 3- to 7-memberbed cyclic amide that may contain, aside from the nitrogen atom, 1 to 3 heteroatoms selected from the group consisting of a nitrogen atom, a sulfur atom, and an oxygen atom.

7. The compound according to claim 2 or a salt thereof, wherein in the formula (1a), n is 3, q in the ring C is 3, and the ring D is represented by the following formula:

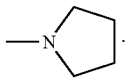

8. The compound according to claim 2 or a salt thereof, wherein in the formula (1a), n is 3, q in the ring C is 3, and $R^1$ and $R^2$ are each independently a hydrogen atom, a methyl group, an ethyl group, an acetyl group, or a methylsulfonyl group.

9. The compound according to claim 2, wherein the compound represented by the formula (1a) is 5-[3,5-bis(trifluoromethyl)benzyl]-6-oxo-7-phenyl- 9-[4-(pyrrolidine-1-yl)piperidine-1-yl]-2,3,4,5-tetrahydro-6H-pyrido[2,3-b][1,5]oxazocine.

10. The compound according to claim 2, wherein the compound represented by the formula (1a) is 5-[3,5-bis(trifluoromethyl)benzyl]-7-(4-fluorophenyl)-6-oxo-9-[4-(pyrrolidine-1-yl)piperidine-1-yl]-2,3,4,5-tetrahydro-6H-pyrido[2,3-b][1,5]oxazocine.

11. The compound according to claim 2, wherein the compound represented by the formula (1a) is 5-[3,5-bis(trifluoromethyl)benzyl]-7-(2-methylphenyl)-6-oxo-9-[4-(pyrrolidine-1-yl)piperidine-1-yl]-2,3,4,5-tetrahydro-6H-pyrido [2,3-b][1,5]oxazocine.

12. A method of treating dysuria, which comprises administering a therapeutically effective amount of a compound according to claim 1 or a salt thereof to a patient in need thereof.

13. A pharmaceutical composition containing a compound according to claim 1 or a salt thereof as active ingredient, and one or more pharmaceutically acceptable adjuvants.

14. A pharmaceutical composition containing a compound according to claim 2 or a salt thereof as active ingredient, and one or more pharmaceutically acceptable adjuvants.

15. The method according to claim 12, wherein the dysuria is increased urinary frequency or incontinence of urine.

* * * * *